United States Patent
Joo et al.

(10) Patent No.: US 10,653,534 B2
(45) Date of Patent: May 19, 2020

(54) ACETABULAR CUP DETACHING APPARATUS FOR ARTIFICIAL HIP JOINT

(71) Applicant: IMEDICOM, Gunpo-si, Gyeonggi-do (KR)

(72) Inventors: Don-Soo Joo, Gunpo-si (KR); Dong-Su Back, Gunpo-si (KR)

(73) Assignee: IMEDICOM, Gunpo-si, Gyeonggi-Do (KR)

( * ) Notice: Subject to any disclaimer, the term of this patent is extended or adjusted under 35 U.S.C. 154(b) by 257 days.

(21) Appl. No.: 15/743,543

(22) PCT Filed: Jun. 24, 2016

(86) PCT No.: PCT/KR2016/006794
§ 371 (c)(1),
(2) Date: Jan. 10, 2018

(87) PCT Pub. No.: WO2017/022950
PCT Pub. Date: Feb. 9, 2017

(65) Prior Publication Data
US 2018/0200073 A1     Jul. 19, 2018

(30) Foreign Application Priority Data

Jul. 31, 2015   (KR) .................. 10-2015-0109103
Feb. 26, 2016   (KR) .................. 10-2016-0023457

(51) Int. Cl.
*A61F 2/46*        (2006.01)

(52) U.S. Cl.
CPC .............. *A61F 2/4609* (2013.01); *A61F 2/46* (2013.01); *A61F 2/4603* (2013.01); *A61F 2002/4619* (2013.01)

(58) Field of Classification Search
CPC ........ A61F 2/46; A61F 2/4603; A61F 2/4609; A61F 2002/4623; A61F 2002/4624; A61F 2002/4625; A61F 2002/4681
(Continued)

(56) References Cited

U.S. PATENT DOCUMENTS

| 65,114 A | * | 5/1867 | Perkins ................... G05G 1/12 |
| | | | 74/548 |
| 1,428,840 A | * | 9/1922 | Gates .................... B25B 13/466 |
| | | | 81/63.2 |

(Continued)

FOREIGN PATENT DOCUMENTS

| KR | 10-1402893 B1 | 6/2014 |
| WO | WO-2014/110517 A1 | 7/2014 |
| WO | WO-2014/133536 A1 | 9/2014 |

*Primary Examiner* — Eric S Gibson
(74) *Attorney, Agent, or Firm* — Rabin & Berdo, P.C.

(57) ABSTRACT

An acetabular cup detaching apparatus for an artificial hip joint, according to an embodiment of the present invention, comprises: a body part that rotates with power transmitted thereto; and a cutting part brought in close contact with the inner circumferential surface of the acetabular cup and rotating together with the body part to cut the surface of the acetabular cup. According to the present invention, an operation can be easily performed by rotating a blade, together with a rotary shaft part, along the outer circumferential surface of the acetabular cup in the radial direction of the acetabular cup through electric control, which makes it possible to rapidly and accurately detach the acetabular cup from an acetabular bone irrespective of an operator's skill. In addition, it is possible to prevent damage to the blade in advance, minimize damage to an acetabular bone, and accurately detach only the acetabular cup from the acetabular bone by forming a supporting cup and the blade in sizes corresponding to the outer circumferential surface and inner circumferential surface of the acetabular cup and gradually (Continued)

cutting the acetabular bone part, to which the acetabular cup is attached, by rotating the blade at a predetermined angle according to predetermined steps.

32 Claims, 24 Drawing Sheets

(58) Field of Classification Search
USPC .................................................. 606/99, 100
See application file for complete search history.

(56) References Cited

U.S. PATENT DOCUMENTS

| | | | | |
|---|---|---|---|---|
| 1,457,570 | A * | 6/1923 | Guthard | B25G 1/005 81/177.5 |
| 1,683,384 | A * | 9/1928 | Durham, Jr. | B25B 23/0035 81/177.5 |
| 1,741,969 | A * | 12/1929 | Bellows | B25B 23/0035 81/177.5 |
| 3,738,768 | A * | 6/1973 | Kuhn | B25B 13/44 408/240 |
| 4,729,270 | A * | 3/1988 | Pritchard | B25B 13/00 81/177.5 |
| 6,260,452 | B1 * | 7/2001 | Yu | B25B 23/0021 81/177.2 |
| 6,565,575 | B2 * | 5/2003 | Lewis | A61B 17/1666 606/99 |
| 7,331,261 | B2 * | 2/2008 | Blizniuk | B25B 23/0035 81/124.4 |
| 7,744,602 | B2 * | 6/2010 | Teeny | A61F 2/4609 606/100 |
| 7,749,227 | B2 * | 7/2010 | Lechot | A61B 17/1631 606/104 |
| 7,785,331 | B2 * | 8/2010 | Leisinger | A61F 2/4637 606/91 |
| 7,927,376 | B2 * | 4/2011 | Leisinger | A61F 2/4637 606/91 |
| 7,998,146 | B2 * | 8/2011 | Anderson | A61B 17/1666 606/91 |
| 8,435,244 | B2 * | 5/2013 | Meek | A61F 2/38 606/86 R |
| 8,475,460 | B1 * | 7/2013 | Roger | A61B 17/1666 606/80 |
| 8,834,471 | B2 * | 9/2014 | Roger | A61B 17/1666 606/80 |
| 8,834,480 | B2 * | 9/2014 | Hudak, Jr. | A61F 2/4609 606/86 R |
| 9,615,941 | B2 * | 4/2017 | Meek | A61F 2/38 |
| 2002/0116007 | A1 * | 8/2002 | Lewis | A61B 17/1666 606/99 |
| 2005/0252348 | A1 * | 11/2005 | Ting | B25B 13/06 81/177.5 |
| 2006/0200165 | A1 * | 9/2006 | Tulkis | A61B 17/1666 606/99 |
| 2007/0010825 | A1 * | 1/2007 | Leisinger | A61F 2/4637 606/99 |
| 2008/0195111 | A1 * | 8/2008 | Anderson | A61B 17/1666 606/90 |
| 2008/0275457 | A1 * | 11/2008 | Meek | A61F 2/38 606/99 |
| 2009/0216240 | A1 * | 8/2009 | Posdal | A61F 2/4609 606/99 |
| 2009/0281550 | A1 * | 11/2009 | Keller | A61F 2/4609 606/99 |
| 2010/0049327 | A1 * | 2/2010 | Isch | A61F 2/34 623/19.12 |
| 2010/0191246 | A1 * | 7/2010 | Howald | A61F 2/34 606/91 |
| 2010/0249796 | A1 * | 9/2010 | Nycz | A61F 2/4609 606/99 |
| 2011/0270254 | A1 * | 11/2011 | Anderson | A61B 17/1666 606/79 |
| 2012/0167726 | A1 * | 7/2012 | Cheng | B25B 23/0021 81/177.5 |
| 2012/0184964 | A1 * | 7/2012 | Hudak, Jr. | A61F 2/4609 606/91 |
| 2013/0331849 | A1 * | 12/2013 | Splieth | A61B 17/92 606/99 |
| 2015/0196402 | A1 * | 7/2015 | Kim | A61F 2/4609 606/81 |
| 2015/0250614 | A1 * | 9/2015 | Davenport | A61F 2/4609 606/99 |
| 2015/0282856 | A1 * | 10/2015 | Haiat | A61F 2/4609 606/100 |
| 2015/0313722 | A1 * | 11/2015 | Hudak, Jr. | A61F 2/4609 606/99 |
| 2015/0359641 | A1 * | 12/2015 | Nic | A61F 2/4609 606/81 |
| 2016/0100957 | A1 * | 4/2016 | Lewis | A61F 2/4609 606/84 |
| 2018/0200073 | A1 * | 7/2018 | Joo | A61F 2/34 |

* cited by examiner (a)

(b)

(a)

(b)

ACETABULAR CUP DETACHING APPARATUS FOR ARTIFICIAL HIP JOINT

TECHNICAL FIELD

The present disclosure relates to an acetabular cup detaching apparatus for an artificial hip joint.

BACKGROUND ART

The artificial hip joint is one of the artificial joints inserted into the hip joint of a patient who is unable to use his or her hip joint due to breakage or wear of the hip joint, and it serves as a joint to enable the patent to maintain his or her usual way of activity.

The artificial hip joint consists of three major parts. That is, it is divided into: first, a first hemispherical acetabular cup provided with a liner on an inner circumferential surface, which is inserted into an acetabular portion of the pelvis and serving as a bearing for the femoral head between the femoral head and the acetabular cup; second, a stem inserted into the femoral head; and finally, a hemispherical head that replaces the femoral head.

Therefore, for patients with pain in the hip joint that is not functioning properly due to arthritis or dysplasia, trauma or infection sequelae, the part of the hip joint that suffers pain can be removed and the removed part can be replaced with the artificial hip joint mentioned above to thus restore the movement function of the joint and eliminate the pain.

Meanwhile, the artificial hip joint wears out as it is used for a long of time.

Particularly, the acetabular cup rubbing against the head has a high incidence of abrasion due to continuous use of the joint, and if the abrasion continues, in a severe case, osteolysis occurs around the acetabular bone with the acetabular cup inserted.

Therefore, it is necessary to remove the existing inserted acetabular cup from the acetabular bone and replace it with a new acetabular cup, and conventionally, in order to remove the acetabular cup from the acetabular bone, a separate tool having an annular cutting edge at a front end is brought into close contact with the inner surface of the acetabular cup, and the user manually rotates the tool to insert the cutting edge between the acetabular cup and the acetabular bone, and then lift up the tool on the cutting edge serving as a main axis to separate the acetabular cup from the acetabular bone.

However, the above-mentioned method has a shortcoming in that the acetabular bone is excessively cut and lost more than necessary in the process of detaching the acetabular cup, and the acetabular bone is directly exposed to the impact, thus having secondary damages.

In addition, it is also disadvantageous in that since the operator manipulates the tool directly, cutting is not uniform and it is also difficult to perform the operation with uniform force or range particularly when an inexperienced operator is performing the operation.

Prior Art Documents

1) U.S. Pat. No. 6,565,575

DISCLOSURE

Technical Problem

The present invention has been made to solve the problems mentioned above, and it is an object of the present invention to provide an acetabular cup detaching apparatus for an artificial hip joint, in which electric control allows precise control irrespective of skill of an operator, and which, when driven, can detach only the acetabular cup precisely from the acetabular bone without affecting the bone, while minimizing the loss of the acetabular bone.

Technical Solution

To achieve the object mentioned above, according to the present disclosure, there is provided an acetabular cup detaching apparatus for an artificial hip joint comprising: a body part that rotates with power transmitted thereto; and a cutting part brought into close contact with an inner circumferential surface of the acetabular cup and rotating together with the body part to cut a surface of acetabular bone to which the acetabular cup attached.

The body part comprises a rotary shaft part formed in a tubular shape that is rotated with power transmitted thereto and having the cutting part coupled to one side; and a housing part surrounding a perimeter of the rotary shaft part.

The cutting part comprises a pivoting cutter coupled to the rotary shaft part and brought into close contact with an inner circumferential surface of the acetabular cup, rotated together with the rotary shaft part in a radial direction of the acetabular cup, and simultaneously rotated along an outer circumferential surface of the acetabular cup to cut a surface of the acetabular bone to which the acetabular cup is attached; a slide moving part disposed slidably on an inner side of the rotary shaft part and moved forward to rotate the pivoting cutter by a predetermined angle while the rotary shaft part is rotating; and an angle adjusting part disposed within the housing part to cause the slide moving part to be slide by a predetermined distance and adjust an angle of rotation of the pivoting cutter.

The pivoting cutter comprises a fixing part coupled to a front end of the rotary shaft part; a pivoting part rotatably coupled to the fixing part; and a supporting cup coupled to a front end of the fixing part and brought into close contact with an inner circumferential surface of the acetabular cup.

The pivoting part comprises a pivoting axis disposed to pass through the fixing part and intersect with a center axis of the fixing part; a pivoting member coupled to the fixing part, with the fixing part being passed through the pivoting shaft, such that the pivoting member is rotatably disposed between the supporting cup and the fixing part, wherein the pivoting member has a rotation guide slot formed in a direction of rotation; a side cover coupled to each of both sides of the pivoting member and rotated together with the pivoting member; a fastening part disposed between the pivoting member and the side cover disposed on both sides of the pivoting member respectively, and rotated together with the side cover; and a blade coupled to the fastening part and rotated together with the fastening part.

The fastening part comprises a supporting plate supported by the side cover; a fastening piece protruding outward from an outer surface of the supporting plate, and having a seating groove formed on an inner side on which the blade is seated and a screw thread formed on an outer side; a locking pin passed through the fastening piece; and a fastening nut fastened to the fastening piece to fix the blade.

The blade comprises a coupling part inserted into the fastening piece along a vertical direction with respect to a center axis of the rotary shaft part, and seated in the seating groove and then rotated forward; and a contacting part extending in an arc shape from the coupling part and comprising a tooth part formed at an end thereof, the contacting part being rotated forward together with the coupling part.

The coupling part comprises a first coupling groove to which the locking pin is inserted when the coupling part is inserted into the fastening piece, and a second coupling groove on which the locking pin disposed in the first coupling groove is seated when the coupling part is rotated forward.

The slide moving part comprises a first slide moving part disposed on an inner side of the rotary shaft part and connected to the angle adjusting part, and moved forward or backward along the inner surface of the rotary shaft part according to an operation of the angle adjusting part; and a second slide moving part disposed on an outer side of the rotary shaft part and connecting the first slide moving part and the pivoting cutter to each other, and pressing the pivoting cutter upon a forward movement of the first slide moving part so that the pivoting cutter is rotated.

The second slide moving part comprises a supporting member coupled to the first slide moving part and linearly moved along an outer circumferential surface of the rotary shaft part; and a pressing member of which one side is coupled to the pivoting cutter and the other side is rotatably coupled to the supporting member, so as to press the pivoting cutter upon a forward movement of the supporting member so that the pivoting cutter is rotated, while simultaneously being rotated outward by an angle corresponding to an angle of rotation of the pivoting cutter.

The angle adjusting part comprises an adjusting lever rotatably disposed on an inner side of the housing part to be rotated forward or backward; and an adjusting part moved forward according to steps according to a rotation of the adjusting lever to rotate the pivoting cutter by a predetermined angle.

The adjusting part comprises a first moving part connected to the adjusting lever, wherein the first moving part is linearly moved forward when the adjusting lever is rotated backward and linearly moved backward when the adjusting lever is rotated forward; a first elastic member disposed in front of the first moving part to elastically support the first moving part; a second moving part disposed on an outer circumferential surface of the rotary shaft part and having a plurality of hooking projections formed along a lengthwise direction; a moving hook rotatably provided on the first moving part to support and move the second moving part forward when the adjusting lever is rotated backward, wherein the moving hook is separated away from the second moving part when the adjusting lever is rotated forward; a third moving part supported by the second moving part and moved forward together with the second moving part, and at the same time, connected to the slide moving part to move the slide moving part forward; a second elastic member disposed in front of the third moving part to elastically support the third moving part; and a fixing hook rotatably provided on the housing part to support the second moving part when the adjusting lever is rotated backward, wherein the fixing hook is separated from the second moving part when the adjusting lever is rotated forward.

The first moving part comprises a first sliding part disposed on an inner circumferential surface of the housing part and having a movement restricting slot formed on an outer circumferential surface into which an assembling pin for connecting the adjusting lever and the first moving part to each other is inserted; a second sliding part disposed on an inner side of the first sliding part and integrally operated with the first sliding part, and having the moving hook disposed on a front side thereof; and a stopper provided on the first sliding part to support the moving hook.

The moving hook is supported by the stopper and held in a horizontal position, and elastically supported with an auxiliary elastic member provided between the moving hook and the first moving part, wherein, when the moving hook is spaced away from the stopper, the moving hook is rotated by the elastic force of the auxiliary elastic member and brought into contact with the second moving part.

The second moving part comprises, on an outer circumferential surface, a supporting projection and the plurality of hooking projections, which support the third moving part and which are hooked on the moving hook before the moving hook is separated from the stopper.

The third moving part comprises a connecting part provided on an outer side of the rotary shaft part; and a connecting pin passed through the connecting part, the rotary shaft part, and the slide moving part to connect the connecting part and the slide moving part.

The fixing hook is supported by the first moving part and held in a horizontal position, and elastically supported with an auxiliary elastic member provided between the fixing hook and the housing part, wherein, when the fixing hook is spaced away from the first moving part, the fixing hook is rotated by the elastic force of the auxiliary elastic member and brought into contact with the second moving part.

The body part comprises a handle part that can be gripped.

The handle part comprises a clamp provided on an outer circumferential surface of the rotary shaft part; and a locking nut fastened to an end of the clamp to fix the clamp.

The clamp comprises a cage surrounding a perimeter of the rotary shaft part; a movement restricting part disposed on an inner side of the cage and brought into close contact with an outer circumferential surface of the rotary shaft part to limit the movement of the clamp when the locking nut is fastened; and a bearing disposed on an inner side of the cage to support the rotary shaft part.

The movement restricting part comprises an anchor disposed on the outer circumferential surface of the rotary shaft part and pressed and brought into close contact with the rotary shaft part when an external force is applied; and a pressing block disposed at both ends of the anchor and pressing the anchor when the locking nut is fastened.

The handle part further comprises an auxiliary handle.

The auxiliary handle comprises a clamp ring that surrounds a perimeter of the handle part upon being rotated; and a grip fastened to the clamp ring.

The body part further comprises a power part coupled to the rotary shaft part to transmit power to the rotary shaft part.

The power part comprises a motor coupled to the rotary shaft part to provide power; a power supply to supply power to the motor; a control button to control an operation of the motor; and a housing to receive the motor and the control button therein.

The fastening parts comprises a fastening body disposed between the pivoting member and the side cover, and having a guide groove formed therein; a cover coupled to one side of the fastening body to form a slot into which the blade can be inserted; a moving member coupled to the guide groove, wherein, when the blade is inserted into the slot, the moving member is pressed against the blade, moved along the guide groove toward the rotary shaft part, and then slid toward the blade and coupled to the blade; a movement restricting member coupled to the other side of the fastening body to restrict the movement of the moving member; and an elastic supporting member disposed between the moving member and the movement restricting member and resiliently supporting the moving member toward the slot.

The fastening parts comprises a fixing pin to fix the moving member and the movement restricting member to the fastening body; and a blade elastic supporting member provided on the fixing pin to elastically support the blade, wherein, when the moving member that fixes the blade is separated away from the blade, the blade elastic supporting member is decompressed to thus press and move the blade in a direction opposite to a direction in which the blade has been inserted.

The fastening body comprises a supporting plate supported by the side cover; and a guide part protruding outward from an outer surface of the support plate, and comprising, on an inner side, the guide groove, a receiving groove for receiving the blade elastic supporting member, and a blade elastic supporting member insertion hole communicating with the receiving groove and into which the one side of the blade elastic supporting member is inserted, and also comprising, on an outer side, a plurality of pin fastening holes passed through the guide groove and the receiving groove.

The moving member comprises a first moving part seated in the guide groove and moved along the guide groove; and a second moving part seated on an end of the fastening body and moved along an end of the fastening body when the first moving part is moved.

The first moving part comprises a movement restricting slot through which the fixing pin is passed, and an elastic supporting member insertion groove into which one side of the elastic supporting member is inserted, and a hooking protrusion formed on one side of the first moving part that faces the blade to fix the blade within the slot, wherein the hooking protrusion includes an inclined surface formed on one side.

The second moving part comprises a gripping protrusion protruding outward from an end thereof to form a projection.

The acetabular cup detaching apparatus comprises a through hole formed on an inner side of the movement restricting member through which the fixing pin is passed; and formed on one side of the movement restricting member that faces the moving member, an elastic supporting member seating groove which the other side of the elastic supporting member is inserted into and seated on, and a movement restricting protrusion protruding from an end thereof by a predetermined length to limit a maximum movement distance of the moving member.

The blade comprises a coupling part inserted into the slot and fixed with the hooking protrusion and then rotated forward; and a contacting part extending in an arc shape from the coupling part and comprising a tooth part formed at an end thereof, the contacting part being rotated forward together with the coupling part.

The coupling part comprises a hooking protrusion coupling groove into which the hooking protrusion is inserted.

Advantageous Effects

The present disclosure gives the following effects. According to the present invention, an operation can be easily performed by rotating a blade, together with a rotary shaft part, along the outer circumferential surface of the acetabular cup in the radial direction of the acetabular cup through electric control, which makes it possible to rapidly and accurately detach the acetabular cup from an acetabular bone irrespective of an operator's skill.

In addition, it is possible to prevent damage to the blade in advance, minimize damage to an acetabular bone, and accurately detach only the acetabular cup from the acetabular bone by forming a supporting cup and the blade in sizes corresponding to the outer circumferential surface and inner circumferential surface of the acetabular cup and gradually cutting the acetabular bone part, to which the acetabular cup is attached, by rotating the blade at a predetermined angle according to predetermined steps.

Further, a slide moving part, which is linearly movable, is provided on the inner side of the rotary shaft part rotated in a radial direction of the acetabular cup, and the slide moving part is moved forward by predetermined steps through the rotation of the lever to adjust the angle of rotation of the blade. As a result, the user is able to easily rotate the blade along the surface of the acetabular cup even during a rotation of the rotary shaft part, and the simplified arrangement of the structure reduces the restriction of the space required at the time of detaching acetabular cup, thereby minimizing the interference with surrounding body tissues.

BRIEF DESCRIPTION OF THE DRAWINGS

The above and other objects, features and advantages of the present disclosure will become more apparent to those of ordinary skill in the art by describing in detail exemplary embodiments thereof with reference to the accompanying drawings, in which.

BEST MODE

Hereinafter, embodiments of the present invention will be described in detail with reference to the accompanying drawings.

Figure 1:
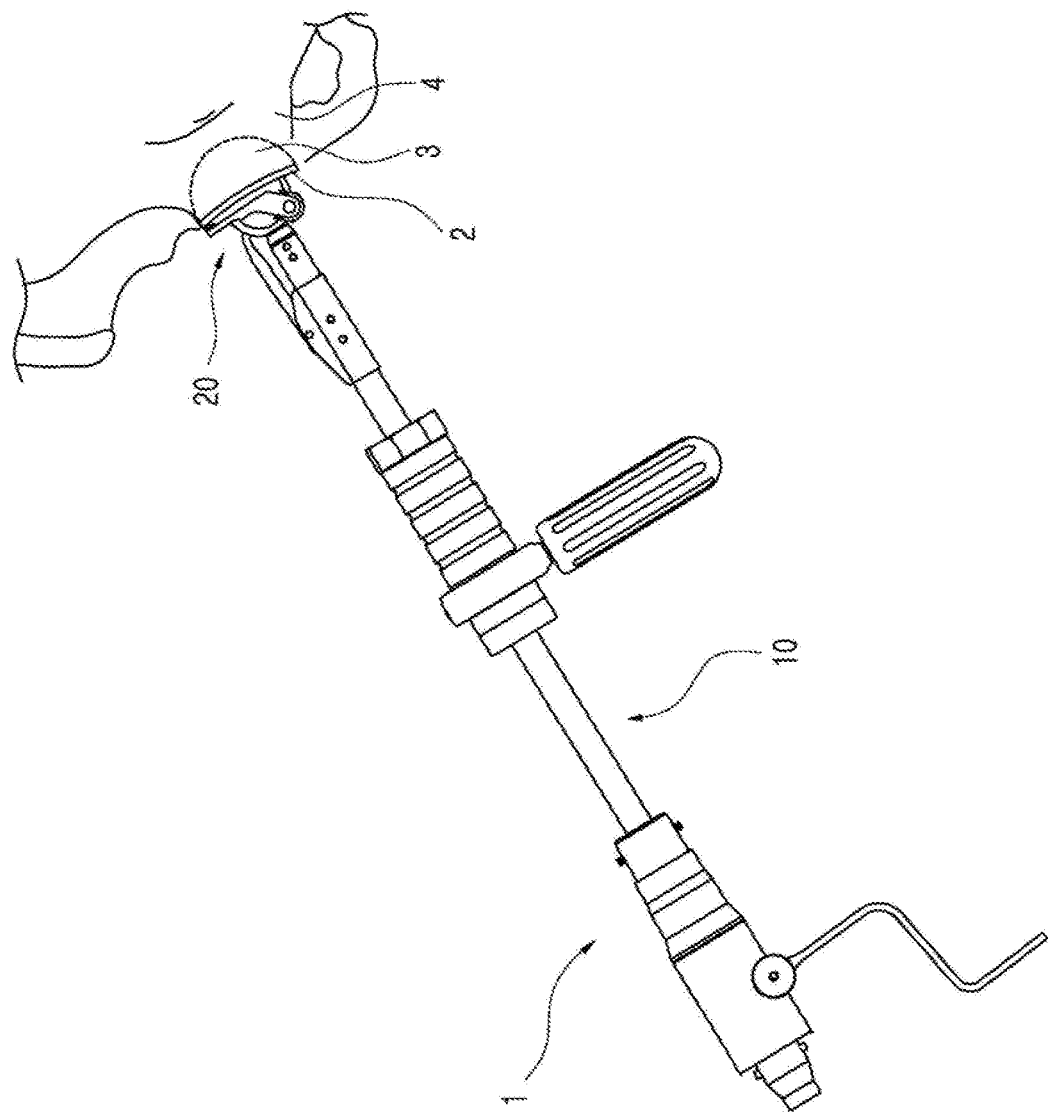
FIG. 1 is a schematic view showing an acetabular cup detaching apparatus for an artificial hip joint in use according to an embodiment.

Referring to FIG. 1, an acetabular cup detaching apparatus 1 for an artificial hip joint according to an embodiment (hereinafter, briefly referred to as "acetabular cup detaching apparatus 1") relates to an apparatus for detaching an acetabular cup 2 inserted into a pelvic bone, which includes: a body part 10 that rotates with power transmitted thereto; and a cutting part 20 in contact with the inner circumferential surface of the acetabular cup 2 and rotates together with the body part 10 to cut the surface 3 of the acetabular bone 20 to which the acetabular cup is attached.

The body part 10 may include a rotary shaft part 11 and a housing part 13.

Figure 2:
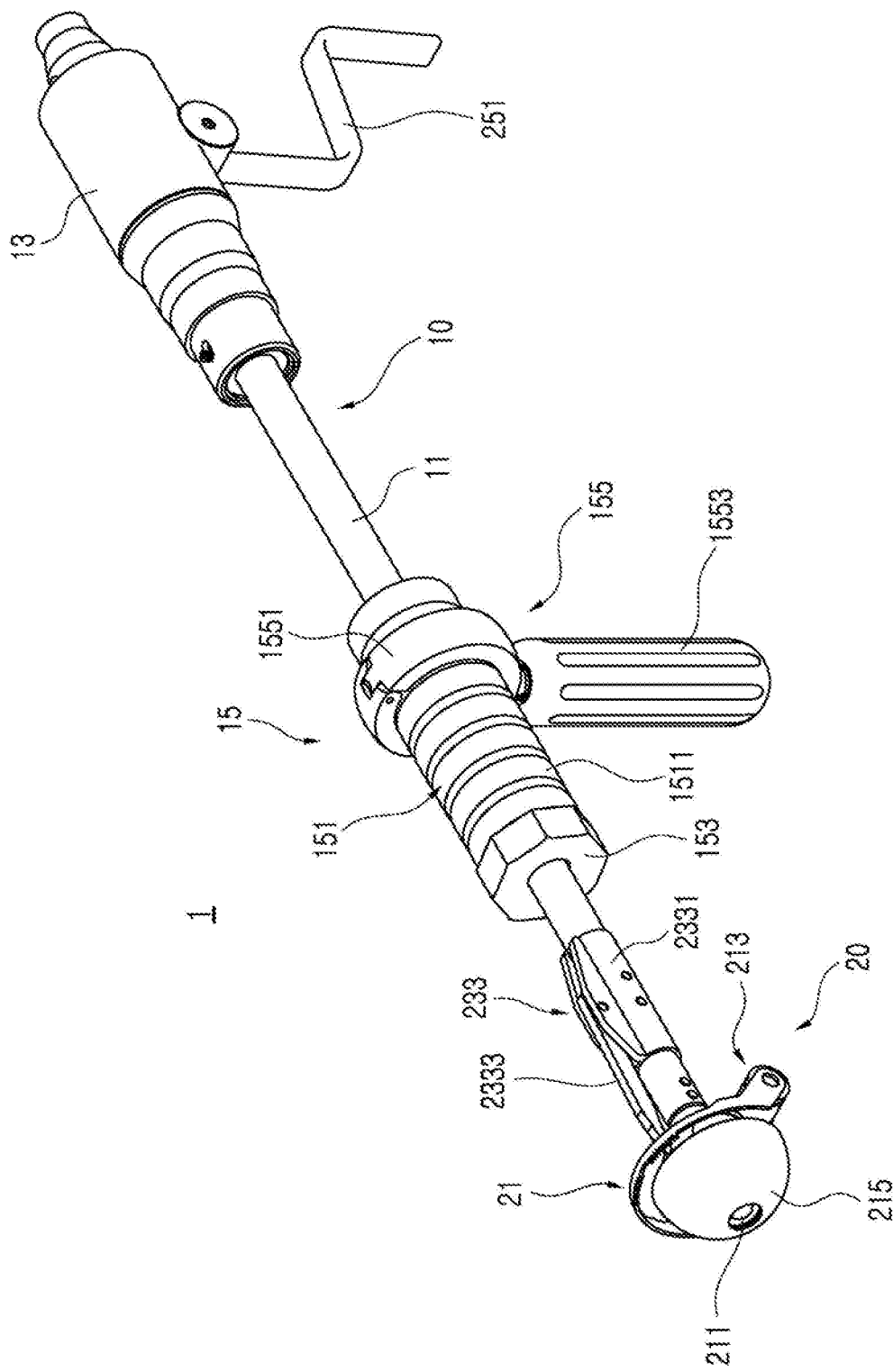
FIG. 2 is a perspective view of an acetabular cup detaching apparatus for an artificial hip joint according to an embodiment.
Figure 3:
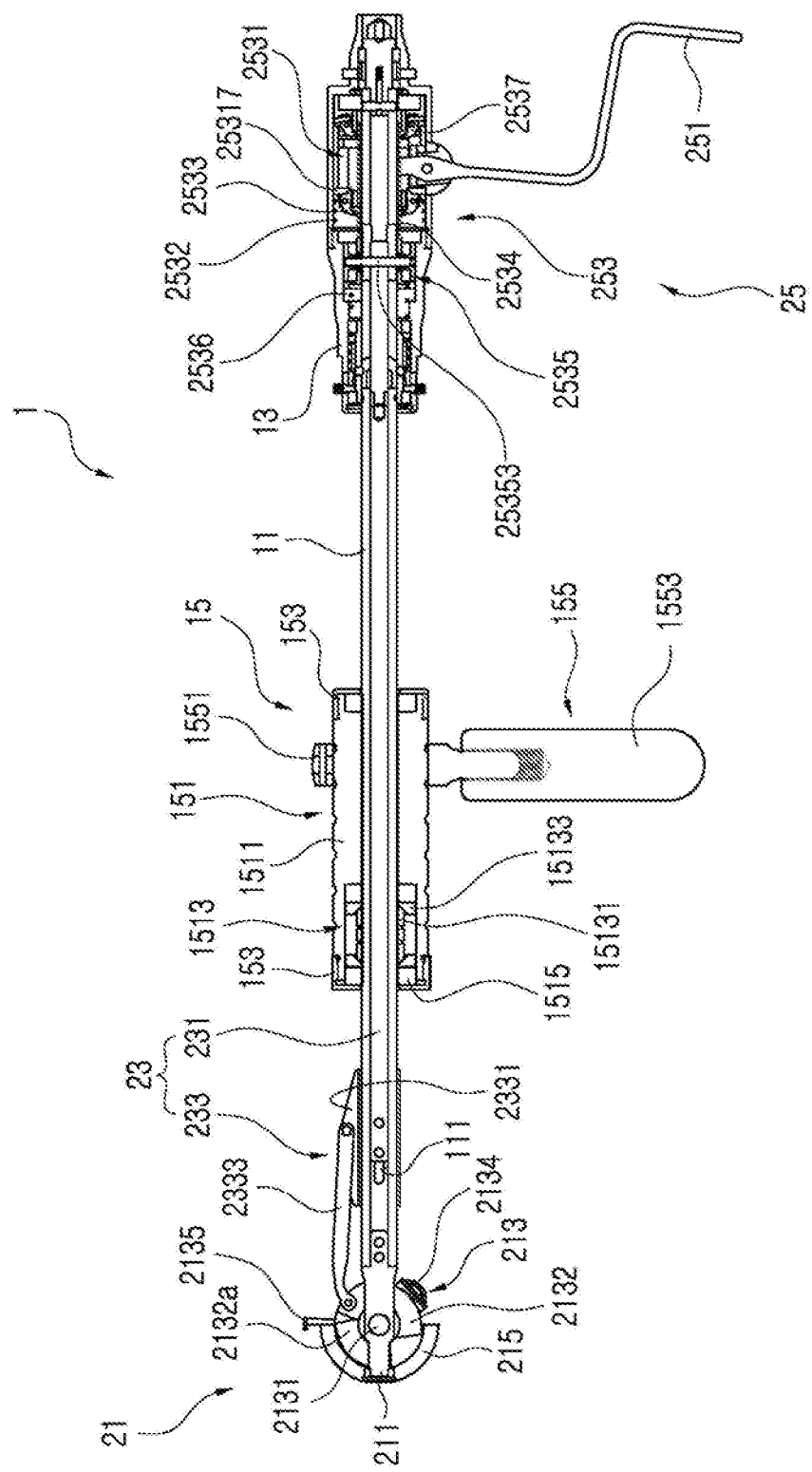
FIG. 3 is a schematic cross-sectional view of an acetabular cup detaching apparatus for an artificial hip joint according to an embodiment.

Referring to FIGS. 2 and 3, the rotary shaft part 11 is formed into a hollow tubular shape and rotated with power transmitted thereto. The cutting part 20 may be coupled to one side of the rotary shaft part 11. In addition, a guide slot 111 may be formed on the outer surface of the rotary shaft part 11 to limit a distance of the linear movement of the cutting part 20, which will be described below.

The housing part 13 may include therein a bearing having the rotary shaft part 11 penetrated therethrough to support the rotary shaft part 11, and may surround the other side of the rotary shaft part 11.

Meanwhile, the cutting part 20 may include a pivoting cutter 21.

Figure 4:
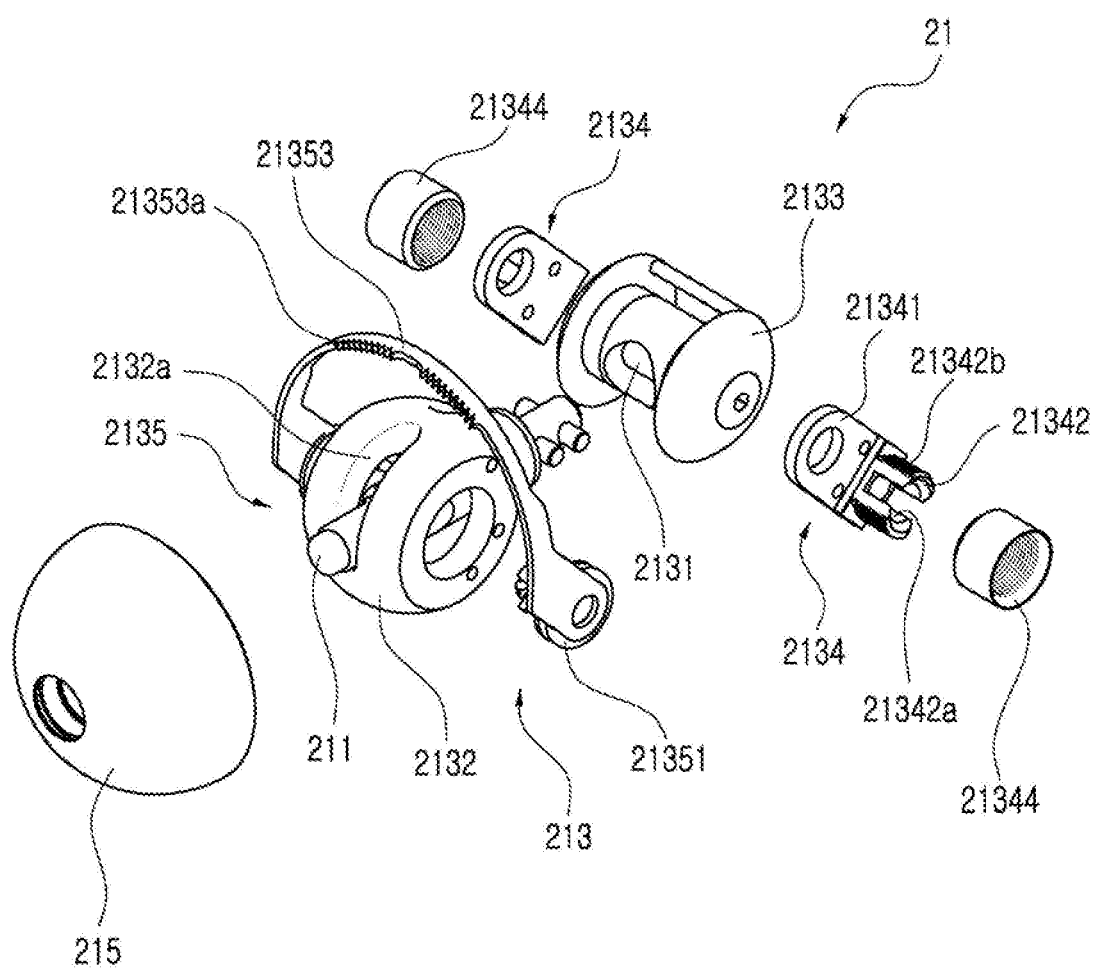
FIG. 4 is a perspective view showing a roughly disassembled state of a pivoting cutter of an acetabular cup detaching apparatus for an artificial hip joint according to an embodiment.
Figure 5:
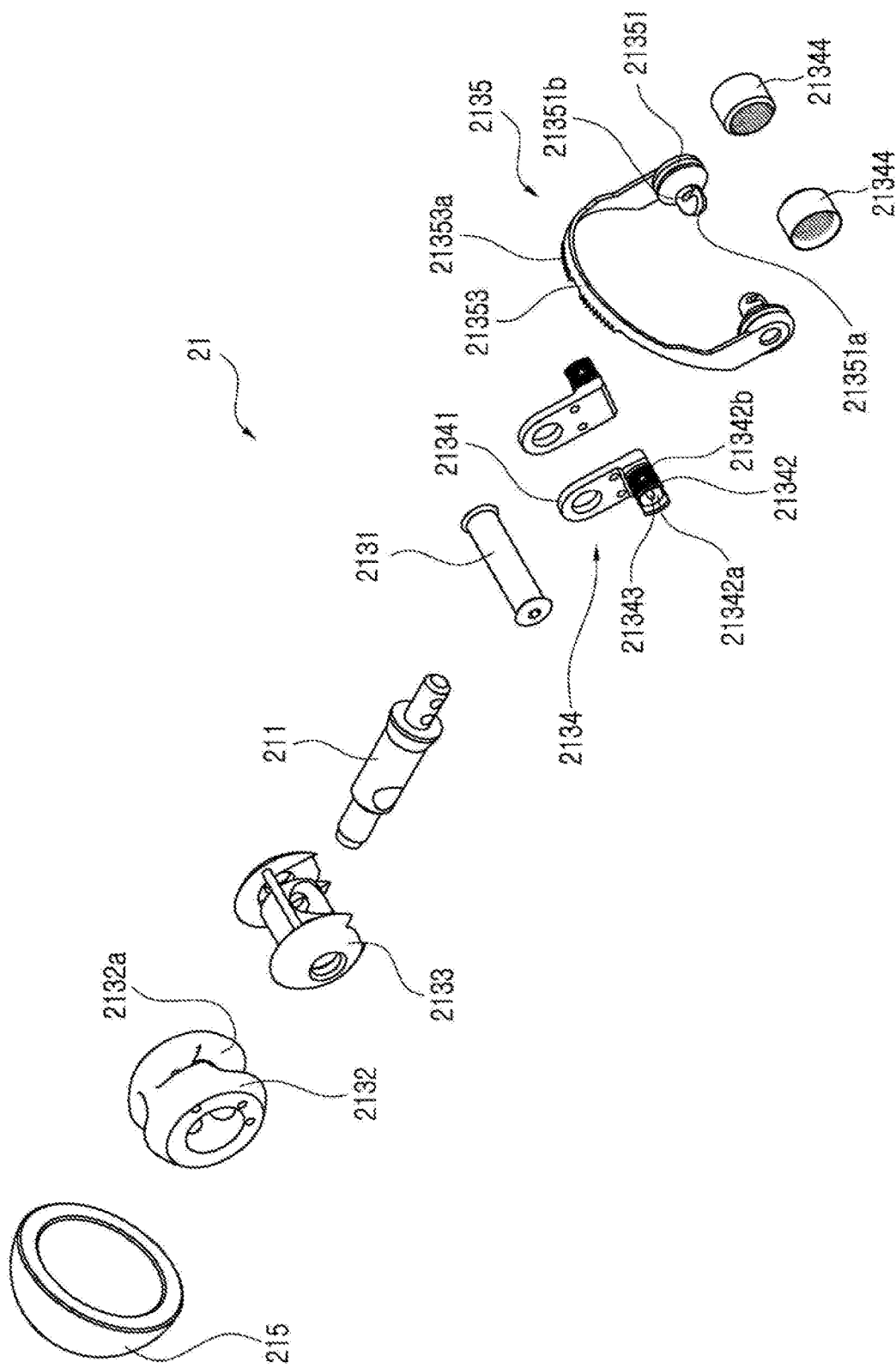
FIG. 5 is a perspective view showing a completely disassembled state of a pivoting cutter of an acetabular cup detaching apparatus for an artificial hip joint according to an embodiment.

Referring to FIGS. 4 and 5, the pivoting cutter 21 is coupled to the rotary shaft part 11 and in close contact with the inner circumferential surface of the acetabular cup 2. The pivoting cutter 21 is rotated in the radial direction of the acetabular cup 2 together with the rotary shaft part 11 and at the same time, it 21 can be rotated along the outer circumferential surface of the acetabular cup 2 to cut the surface 3 of the acetabular bone attached with the acetabular cup 2.

More specifically, the pivoting cutter 21 may include a fixing part 211 coupled to the front end of the rotary shaft part 11 and a pivoting part 213 rotatably coupled to the fixing part 211.

The pivoting part 213 will be described in more detail.

Figure 6:
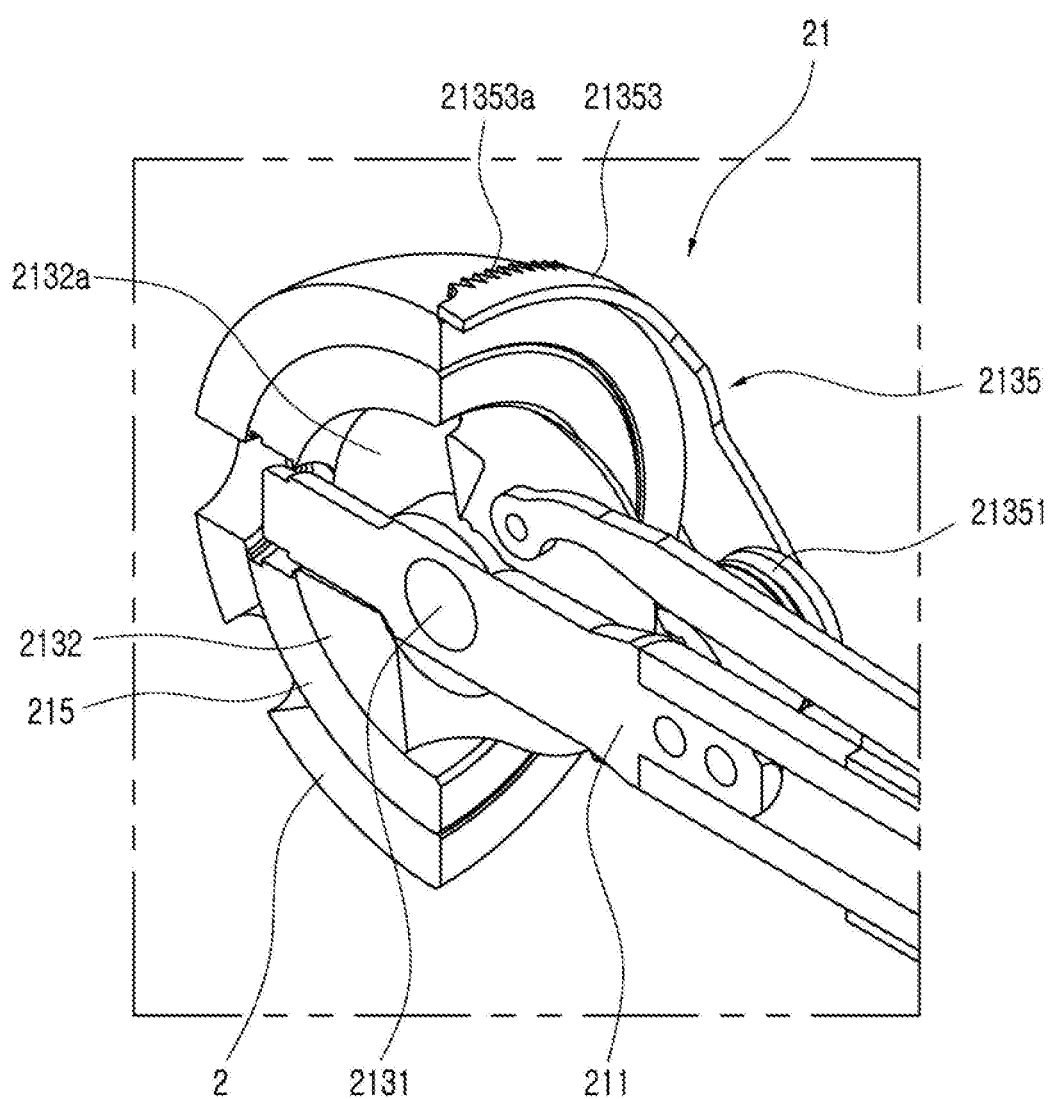
FIG. 6 is a cross-sectional view showing a state in which a pivoting cutter of an acetabular cup detaching apparatus for an artificial hip joint is seated in an acetabular cup according to an embodiment.

Referring to FIGS. 5 and 6, the pivoting part 213 may include a pivoting axis 2131 and a pivoting member 2132. The pivoting axis 2131 is passed through the fixing part 211, while intersecting with the central axis of the fixing part 211, and the pivoting member 2132 is coupled with the fixing part 211, with the fixing part 211 passed through the pivoting axis 2131, to be rotatably disposed between the supporting cup 215 and the fixing part 211. In this example, a rotation guide slot 2132a may be formed around the pivoting member 2132 to limit the distance of rotation in the rotation direction of the pivoting member 2132.

In addition, the pivoting part 213 may include a side cover 2133 coupled to both sides of the pivoting member 2132 to be rotated together with the pivoting member 2132, and a fastening part 2134 disposed between the pivoting member 2132 and the side cover 2133 disposed on both sides of the pivoting member 2132 to be supported by the side cover 2133 and rotated together with the side cover 2133.

Figure 7:
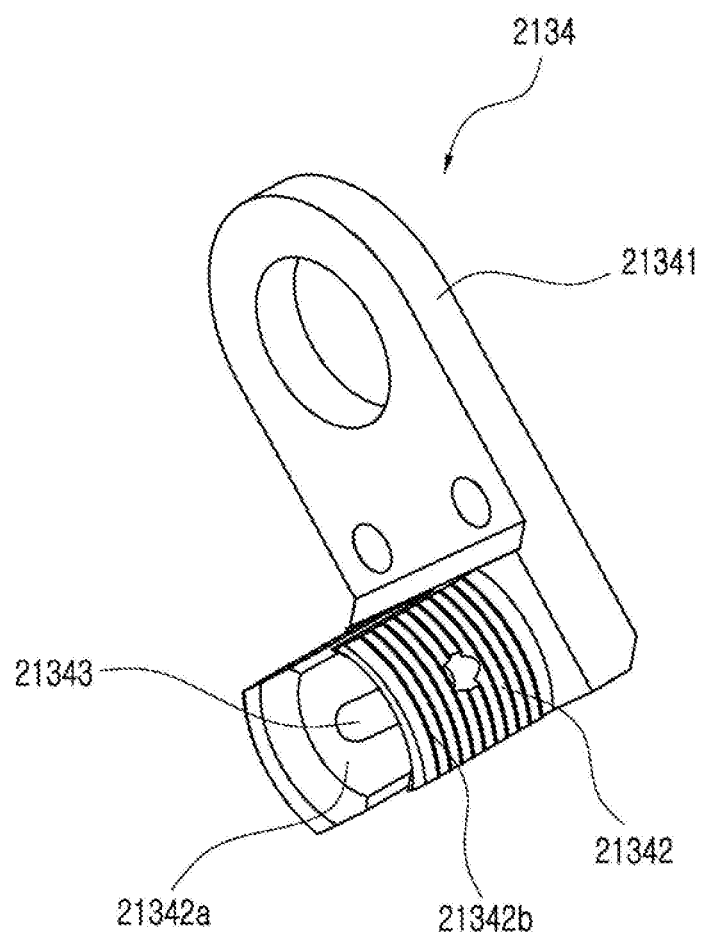
FIG. 7 is a perspective view showing a fastening part of an acetabular cup detaching apparatus for an artificial hip joint according to an embodiment.

Referring to FIG. 7, the fastening part 2134 may include: a supporting plate 21341 inserted between the side cover 2133 and the pivoting member 2132 and supported by the side cover 2133 according to the structure, in which the pivoting shaft 2131 is passed inwardly through the fastening part 2134; a fastening piece 21342 protruding outward from the outer surface of the supporting plate 21341 to be coupled with a blade 2135 to be described later; a locking pin 21343 passed through the fastening piece 21342; and a fastening nut 21344 disposed on the outer side of the fastening part 2134 to press the coupling portion between the blade 2135 and the fastening part 2134 so that the blade 2135 is fixed to the fastening part 2134. In this example, a seating groove 21342a may be formed on an inner side of the fastening piece 21342 so that the blade 2135 is seated thereon, and a thread 21342b may be formed on an outer side of the fastening piece 21342 so that the fastening nut 21344 (to be described below) is fastened therewith.

Further, the pivoting part 213 may include the blade 2135 that is coupled to the fastening part 2134 and rotated together with the fastening part 2134.

Figure 8:
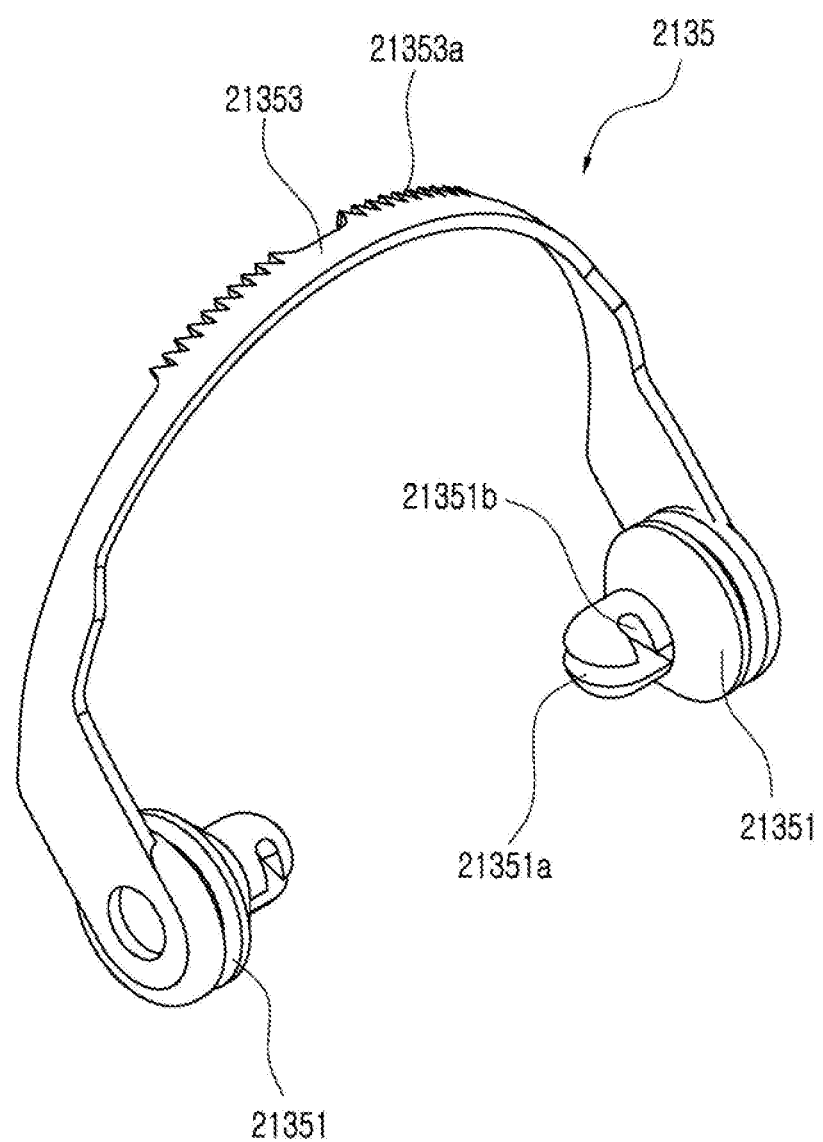
FIG. 8 is a perspective view showing a blade of an acetabular cup detaching apparatus for an artificial hip joint according to an embodiment.

Referring to FIG. 8, the blade 2135 may include a coupling part 21351 inserted into the fastening piece 21342 along a direction perpendicular to the center axis of the rotary shaft part 11 to be seated in the seating groove 21342a and then rotated forward, and a contacting part 21353 extending in an arc shape from the coupling part 21351 and having a tooth part 21353a formed at an end thereof, and rotated forward together with the coupling part 21351 to be moved along the outer circumferential surface of the acetabular cup 2. In this example, the contacting part 21353 may be bent into a shape that corresponds to the outer circumferential surface of the acetabular cup 2 and the tooth part 21353a formed at the end of the contacting part 21353 may include a plurality of teeth formed along the end of the contacting part 21353.

Meanwhile, a groove may be formed in the coupling part 21351.

More specifically, the coupling part 21351 may include a first coupling groove 21351a into which the locking pin 21343 is inserted when the coupling part 21351 is inserted into the engaging piece 21342, and a second coupling groove 21351b on which the locking pin 21343 disposed in the first coupling groove 21351 is seated when the coupling part 21351 is rotated forward.

Figure 9:
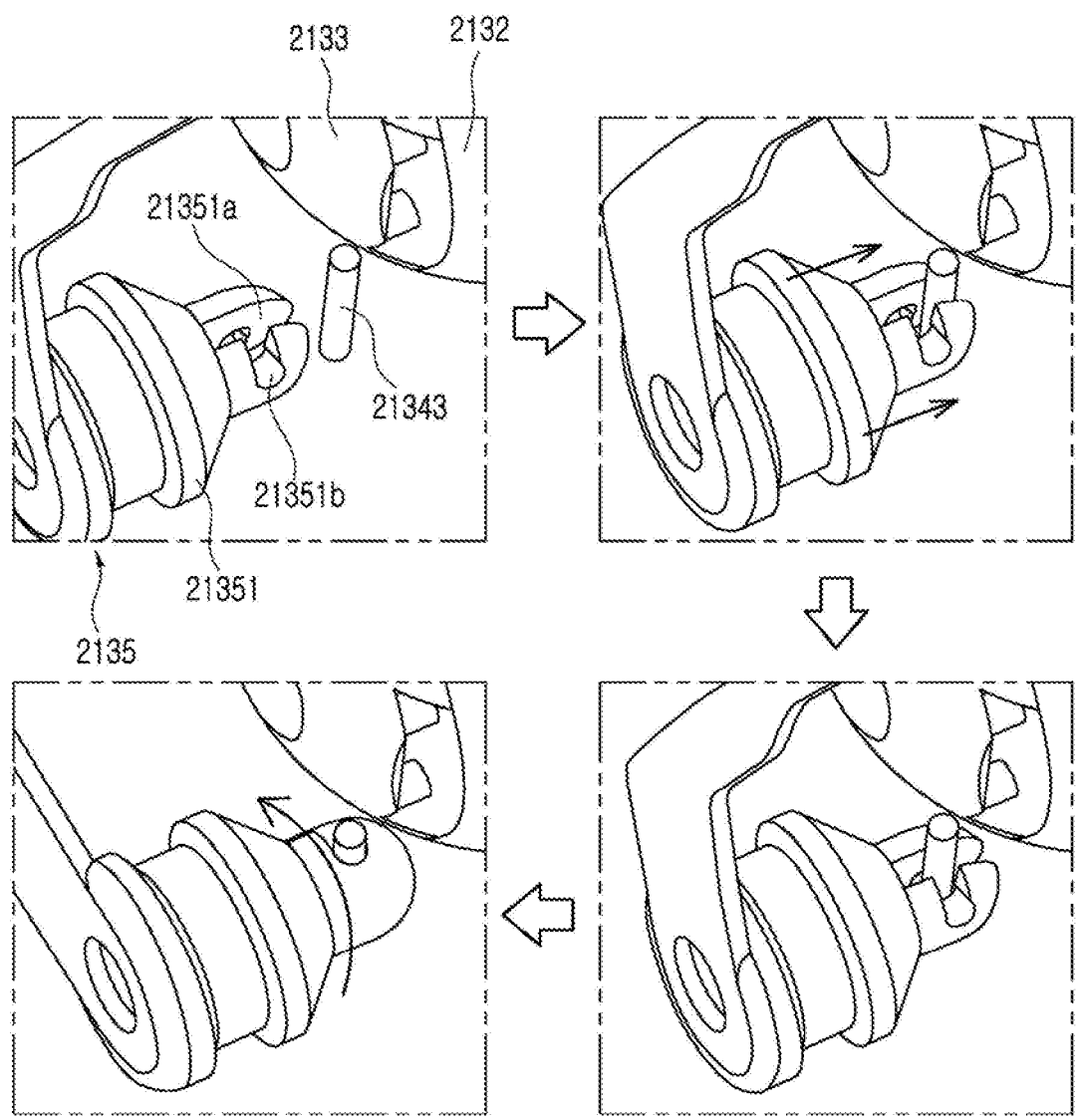
FIG. 9 is a view showing a process of coupling a blade of an acetabular cup detaching apparatus for an artificial hip joint according to an embodiment to a fastening part.

Accordingly, as shown in FIG. 9, the blade 2135 can be coupled to the fastening part 2134 as it 2135 is inserted inwardly to the fastening piece (not shown) so that the locking pin 21343 is inserted into the first coupling groove 21351a, and then rotated so that the locking pin 21343 is seated in the second coupling groove 21351b.

Figure 17:
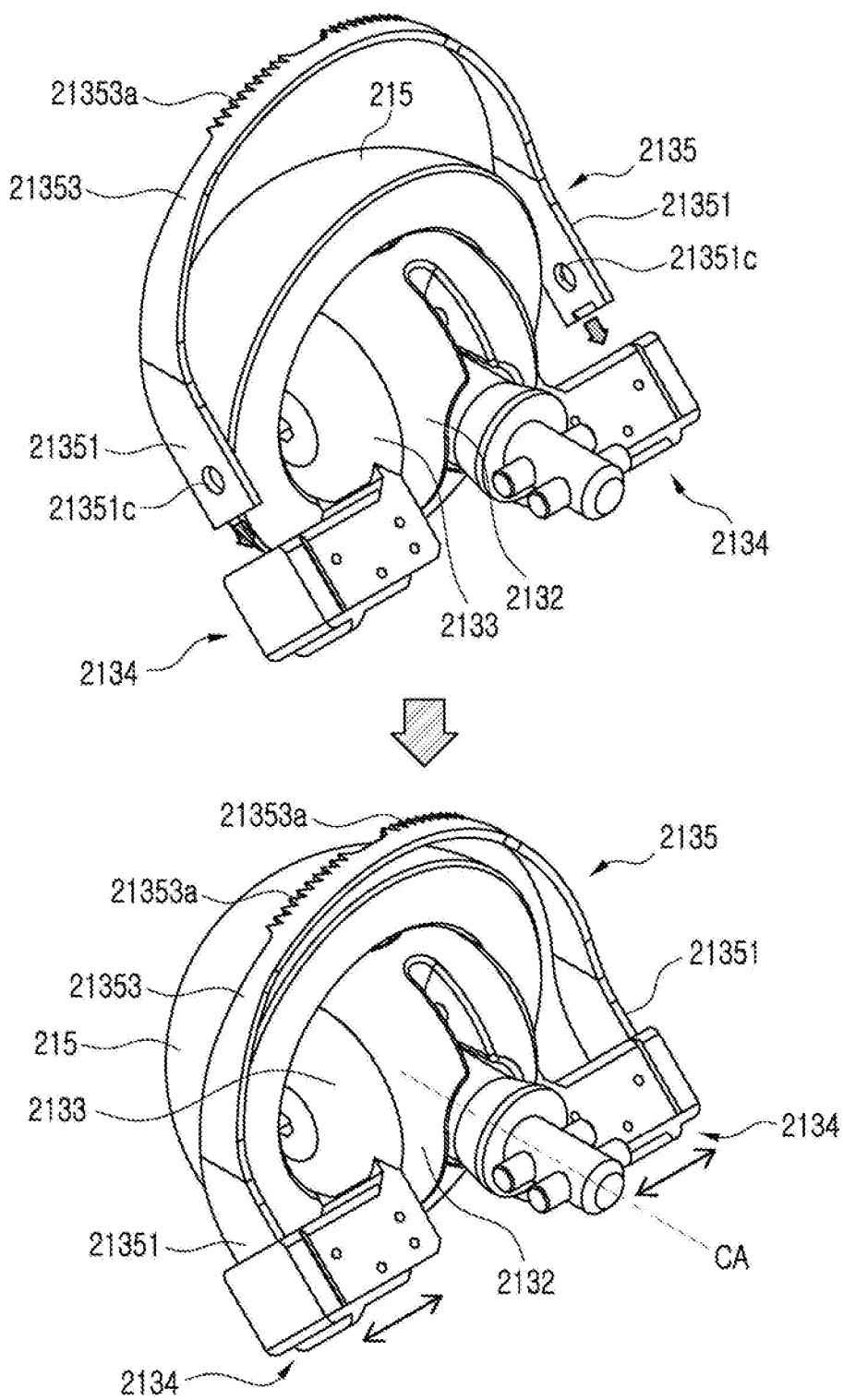
FIG. 17 is a view showing a state in which a blade of the acetabular cup detaching apparatus for an artificial hip joint according to the embodiment of the present invention is coupled to the fastening part in a one-touch manner.

Further, referring to FIG. 17, the fastening part 2134 and the blade 2135 can be coupled in a one-touch manner, in which the blade 2135 can be completely fixed into the fastening part 2134 by the simple process of inserting the blade 2135 into the fastening part 2134.

More specifically, the fastening part 2134 has an insertion space into which the blade 2135 can be inserted and a coupling means provided in the fastening part 2134 to be coupled to the blade 2135 using an elastic force. Accordingly, when the blade 2135 is inserted into the insertion space, the blade 2135 can be pressed with the elastic force and simultaneously coupled to the blade 2135 to retain the blade 2135 in the coupling part 2134. That is, once the blade 2135 is inserted into the fastening piece 21342, the blade 2135 can be completely fixed to the fastening part 2134 only by the process of inserting the blade 2135 into the insertion space formed in the fastening part 2134, without requiring a separate retaining process to fasten the fastening nut 21344 with the fastening piece 21342 and retain the blade 2135 to the fastening part 2134.

Hereinafter, coupling of the fastening part 2134 and the blade 2135 in one-touch manner will be described in more detail.

Figure 18:
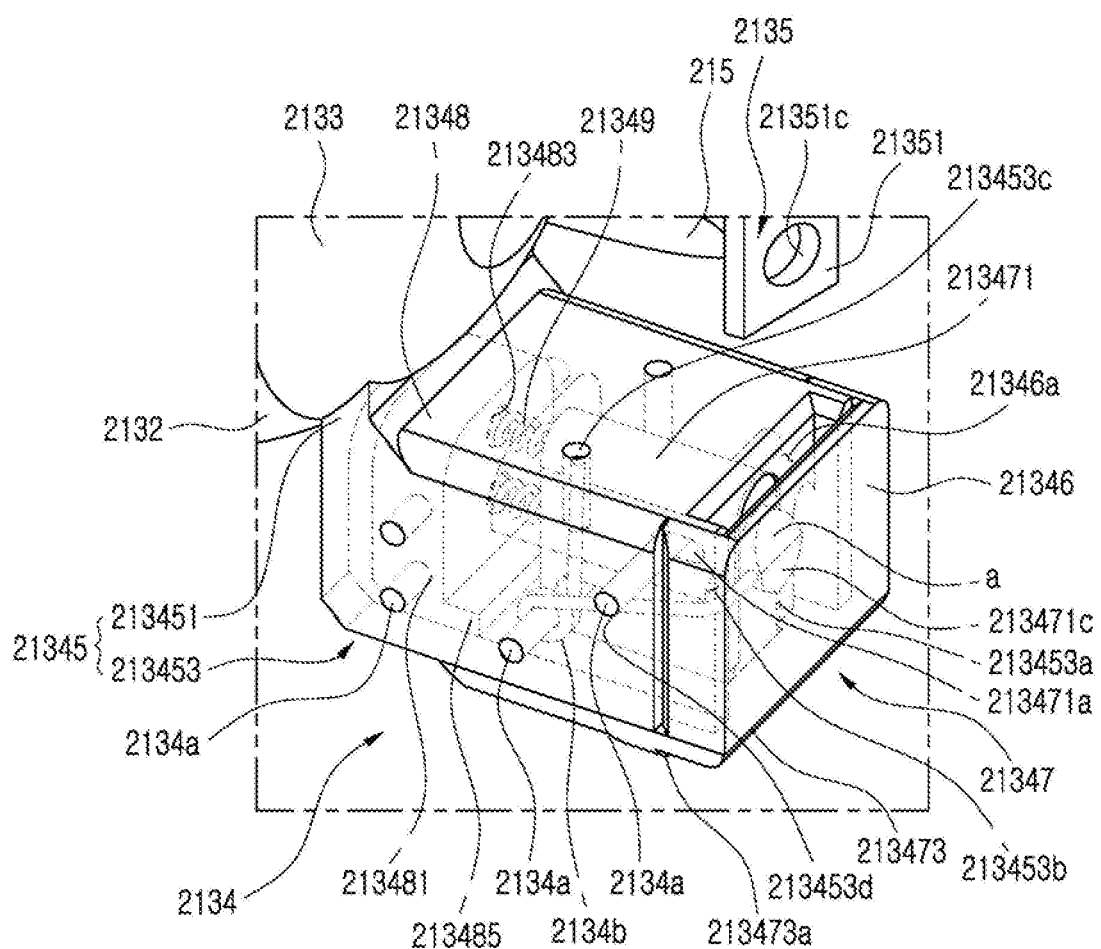
FIG. 18 is a view showing a fastening part to be coupled with a blade of an acetabular cup detaching apparatus for an artificial hip joint according to an embodiment in a one-touch manner.
Figure 19:
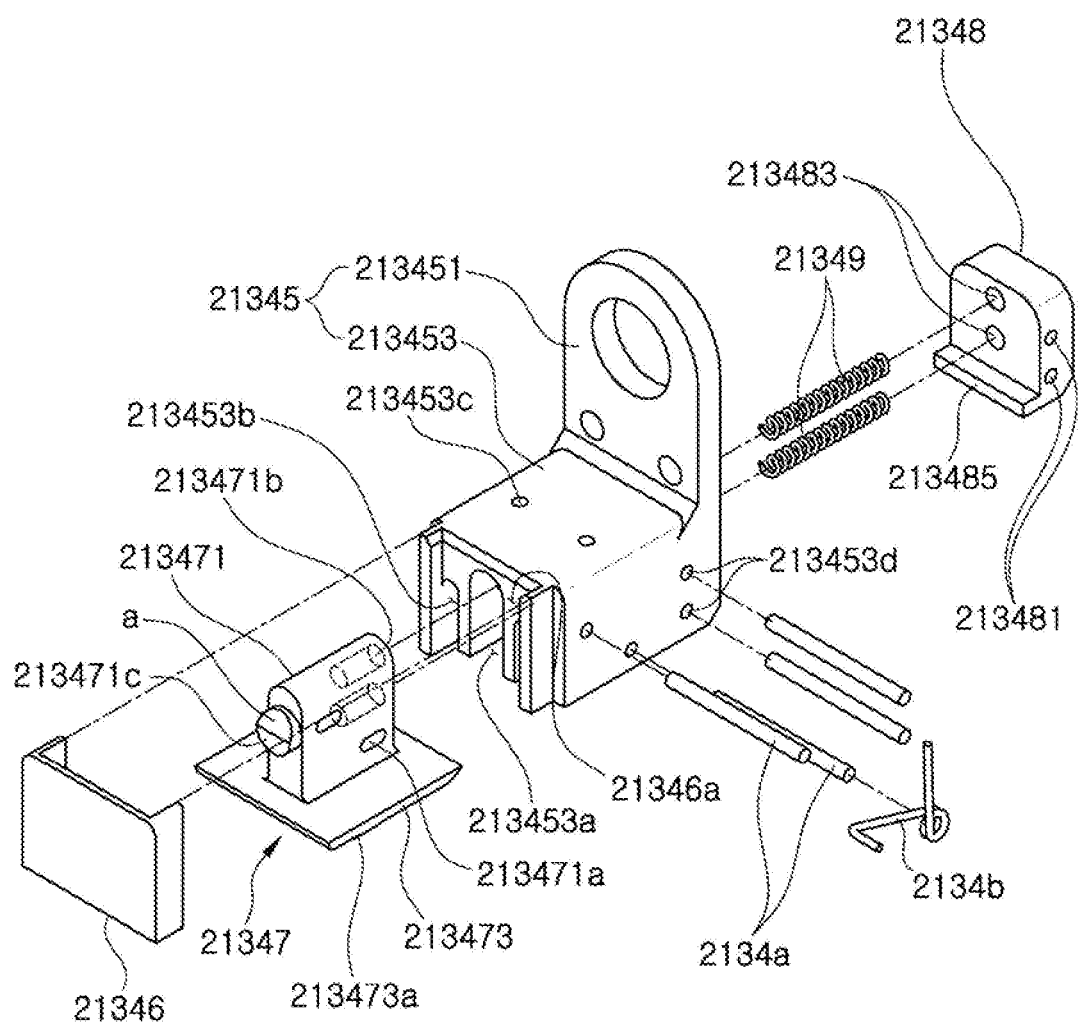
FIG. 19 is an exploded perspective view of a fastening part coupled with a blade of an acetabular cup detaching apparatus for an artificial hip joint according to an embodiment in a one-touch manner.

Referring to FIGS. 17 to 19, the fastening part 2134 may be disposed between the pivoting member 2132 and the side cover 2133, and may include a fastening body 21345 having a guide groove 213453a formed on an inner side thereof along a direction perpendicular to the center axis CA of the rotary shaft part 11, and a cover 21346 coupled to one side of the fastening body 21345 to form a slot 21346a into which the blade 2135 can be inserted.

More specifically, the fastening body 21345 may include a support plate 213451 disposed between the pivoting member 2132 and the side cover 2133 to be supported by the side cover 2133, and a guide part 213453 protruding outward from the outer surface of the support plate 213451 and having a guide groove 213453a formed therein. In addition to the guide groove 213453a, the fastening body 21345 may include, on the inner side thereof, a receiving groove 213453b for receiving the blade elastic supporting member 2134b to be described below, and a blade elastic supporting member insertion hole 213453c in communication with the receiving groove 213453b to receive one side of the blade elastic supporting member 2134b. The guide groove 213453a may also include, on the outer side thereof, a plurality of pin fixing holes 213453d penetrating through the guide groove 213453a and the receiving groove 213453b.

Further, the fastening part 2134 may include a moving member 21347 coupled to the fastening body 21345 to fix the blade 2135.

Figure 20:
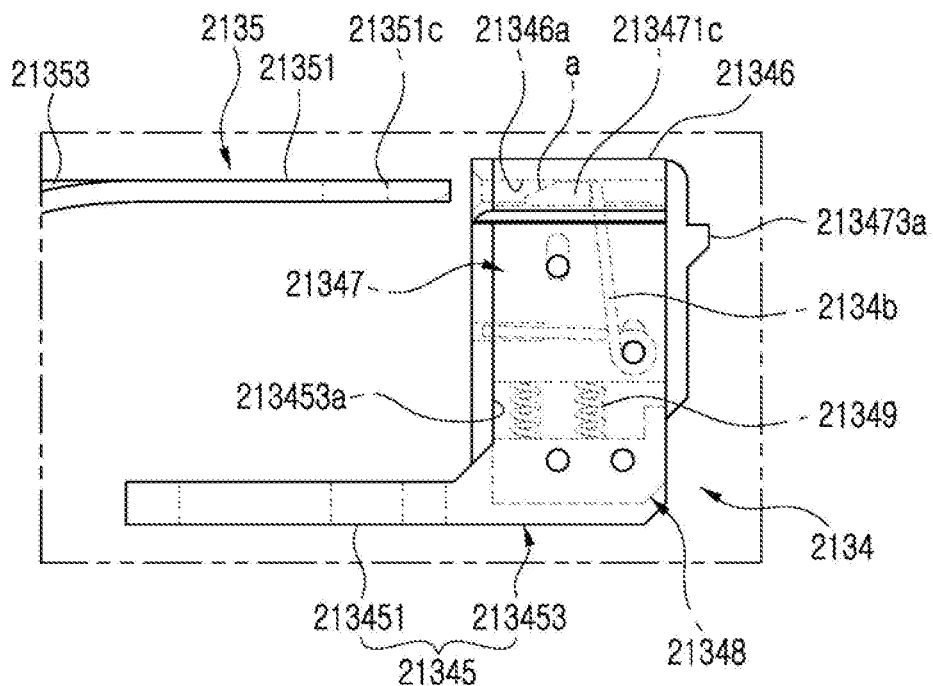
FIGS. 20 to 22 are views schematically showing a coupling process of a fastening part and a blade of an acetabular cup detaching apparatus for an artificial hip joint according to an embodiment.
Figure 20:
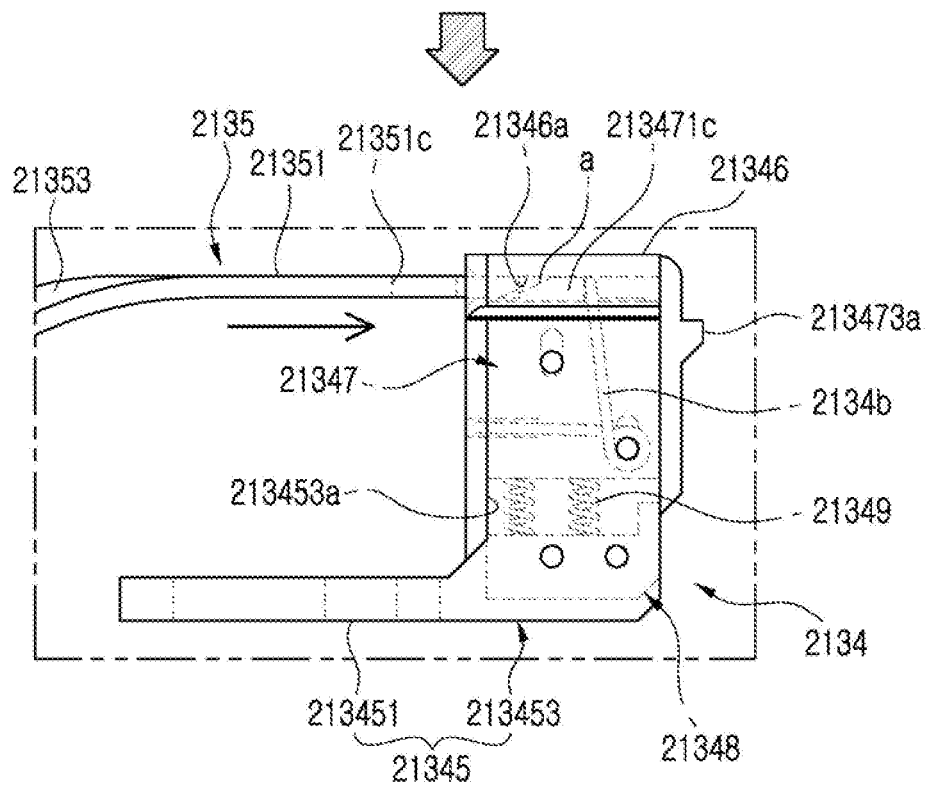
Figure 21:
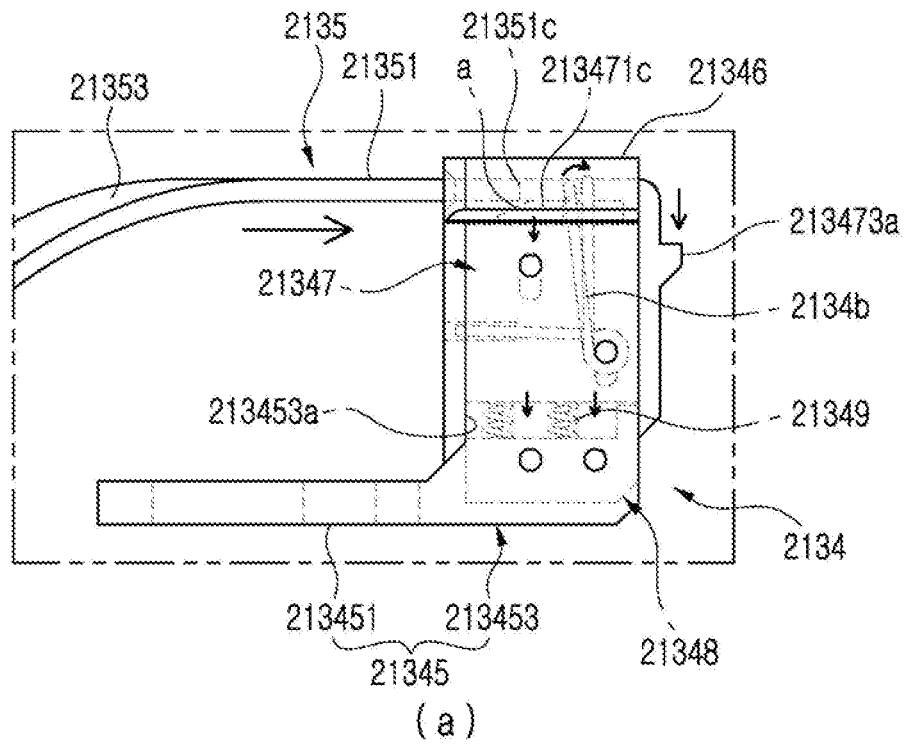
Figure 21:
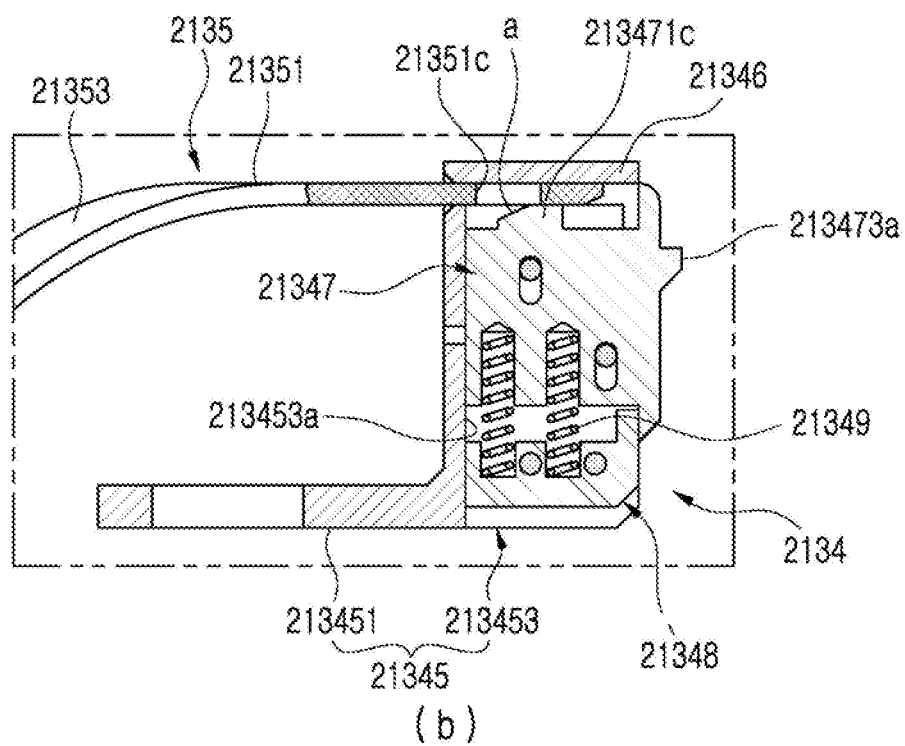
Figure 22:
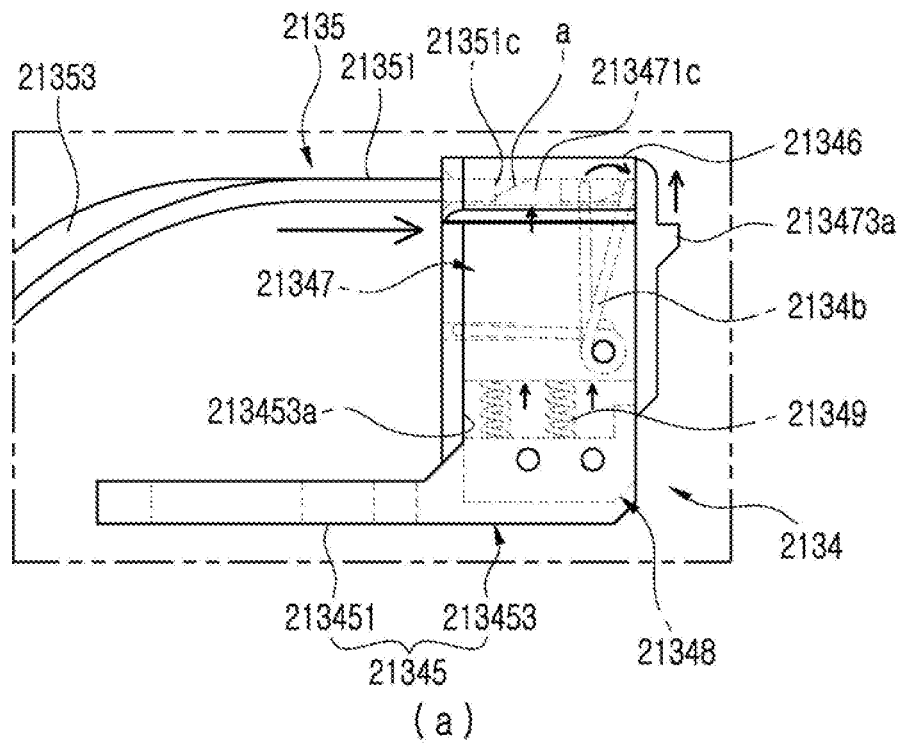
Figure 22:
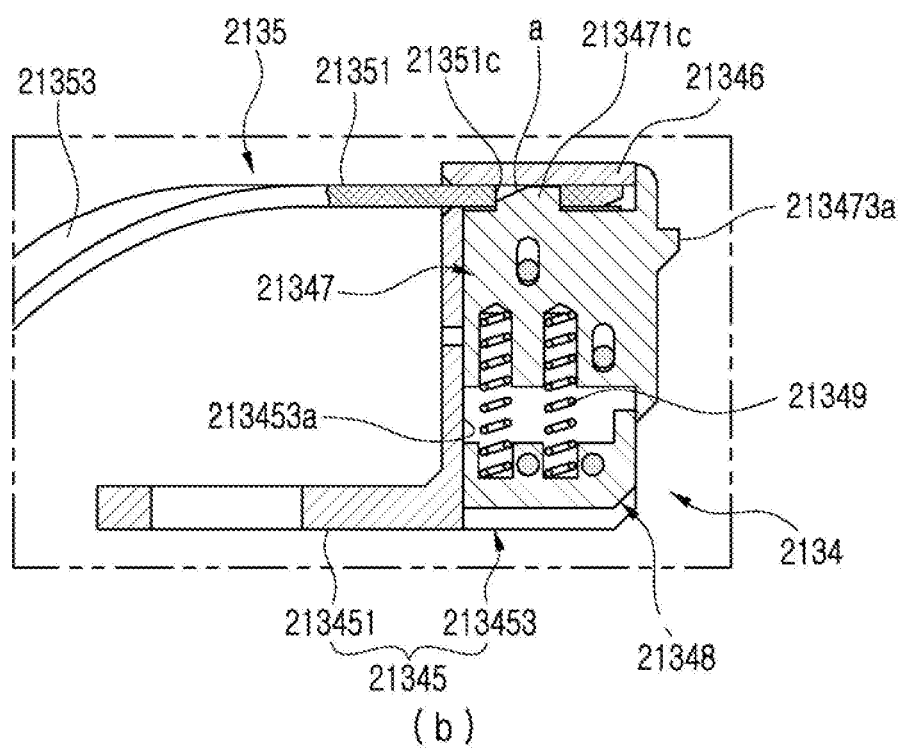

Referring to FIGS. 20 to 22, the moving member 21347 is coupled to the guide groove 213453a of the fastening body 21345, and when the blade 2135 is inserted into the slot 21346a, the moving member 21347 is pressed by the blade 2135 to be slid along the guide groove 213453a toward the rotary shaft part 11, and then slid back toward the blade 2135 to press the blade 2135 and simultaneously coupled to the blade 2135, to thus fix the blade 2135 between the fastening body 21345 and the cover 21346.

As shown in FIGS. 18 and 19, the moving member 21347 may include a first moving part 213471 seated in the guide groove 213453a and moved along the guide groove 213453a, and a second moving part 213473 seated on one end of the fastening body 21345 and moved along the end of the fastening body 21345 when the first moving part 213471 is moved.

The first moving part 213471 is provided with a movement restricting slot 213471a through which a fixing pin 2134a (to be described) is penetrated, and which limits the sliding distance of the first moving part 213471, and an elastic supporting member insertion groove 213471b into which one side of an elastic supporting member 21349 (to be described) is inserted. The first moving part 213471 that faces the blade 2135 may include an inclined surface (a) formed at one side that is brought into contact with the blade 2135 when the blade 2135 is inserted into the slot 21346a, and a hooking protrusion 213471c coupled with the blade 2135 to fix the blade 2135 within the slot 21346a. In addition, the second moving part 213473 may include a gripping protrusion 213473a protruding outward from an end thereof to form a protrusion.

Further, the fastening part 2134 may include a movement restricting member 21348 coupled to the other side of the fastening body 21345 to restrict movement of the moving member 21347, and an elastic supporting member 21349 disposed between the moving member 21347 and the movement restricting member 21348 to elastically urge the moving member 21347 toward the direction of the slot 21346a.

Referring to FIGS. 18 and 19, the movement restricting member 21348 may be disposed opposite to the cover 21346 and coupled to the other side of the fastening body 21345, while having a through hole 213481 therein, through which the fixing pin 2134a for fixing the movement restricting member 21348 to the fastening body 21345 is passed. Further, on one side of the movement restricting member 21348 that faces the moving member 21347, an elastic supporting member seating groove 213483 may be formed, in which the other side of the elastic supporting member 21349 is inserted and seated. Further, a movement restricting projection 213485 may also be formed, which is protruded from the end of the movement restricting member 21348 by a predetermined distance and is in contact with the moving member 21347 to restrict the maximum movement distance of the moving member 21347 so that the moving member 21347 is prevented from being slid toward the movement restricting member 21348 more than a predetermined distance.

Further, the fastening part 2134 may further include a plurality of fixing pins 2134a for fixing the moving member 21347 and the movement restricting member 21348 to the fastening body 21345, and a blade elastic supporting member 2134b that elastically supports the blade 2135.

Figure 23:
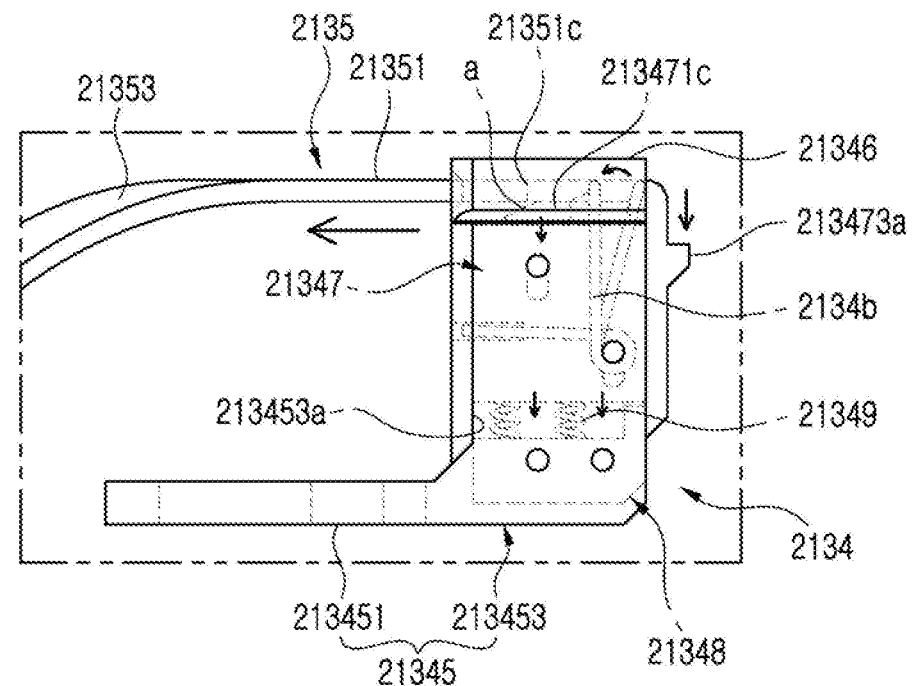
FIGS. 23 and 24 are views schematically showing a process of separating a fastening part from a blade of an acetabular cup detaching apparatus for an artificial hip joint according to an embodiment.
Figure 23:
Figure 23:
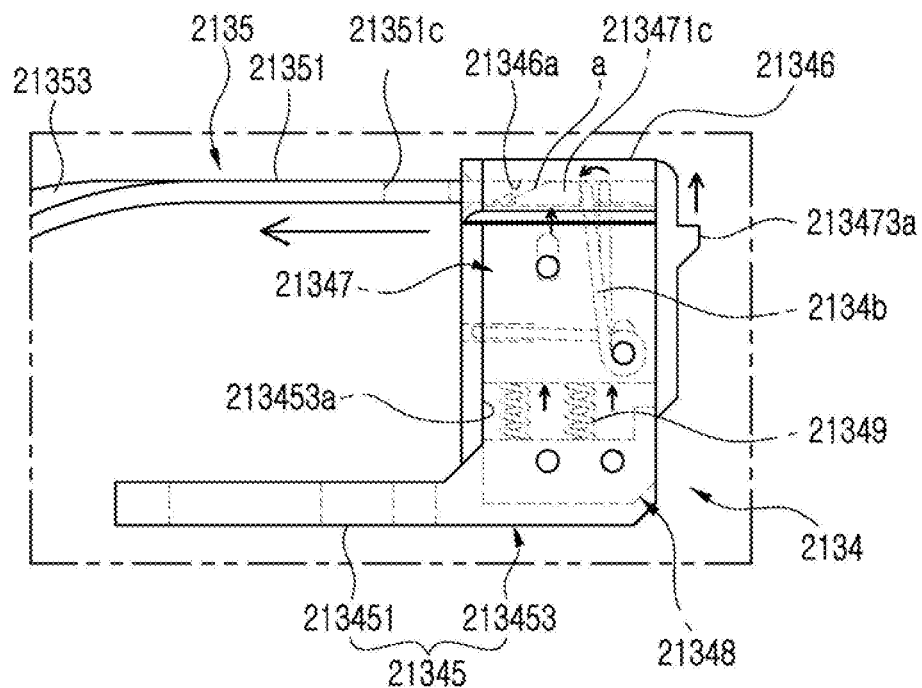
Figure 24:
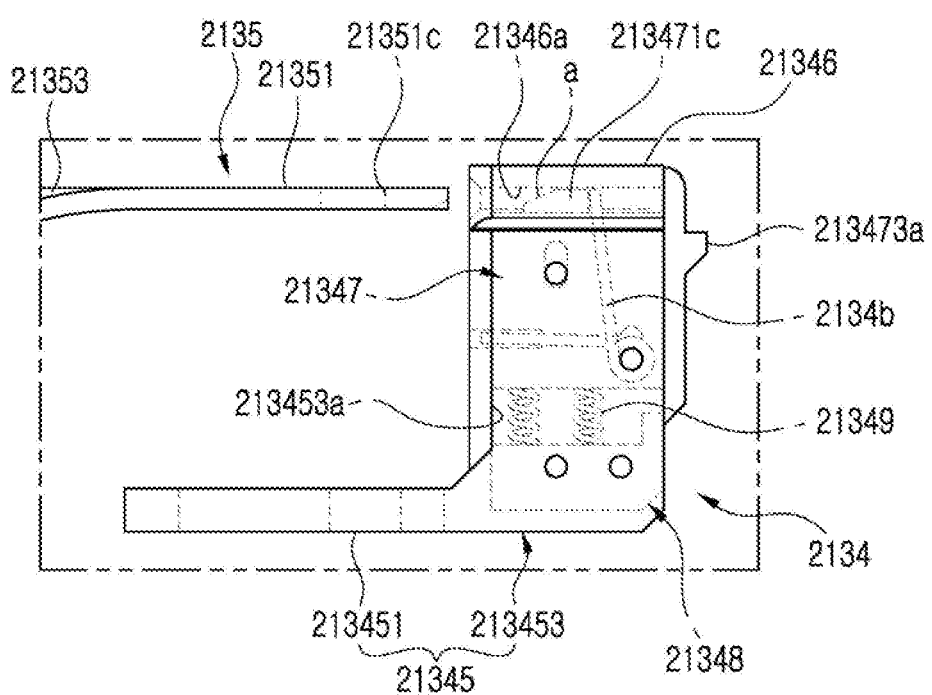

In this example, the blade elastic supporting member 2134b may be assembled with the fixing pin 2134a and disposed in the receiving groove 213453b of the fastening body 21345 in a manner in which one side of the blade elastic supporting member 2134b is inserted into the blade elastic supporting member insertion hole 213453c formed on the inner side of the fastening body 21345, and the other side is pressed against the end of the blade 2135, thereby elastically urging the blade 2135. Accordingly, when the moving member 21347 that fixes the blade 2135 is separated from the blade 2135, as shown in FIGS. 23 and 24, the compression force of the blade elastic supporting member 2134b is ceased so that the blade 2135 pressed, and as a result, the blade 2135 can be moved in a direction opposite the insertion direction of the blade 2135.

Meanwhile, referring to FIGS. 17 and 22, the blade 2135 may include a coupling part 21351 that is inserted into the slot 21346a formed between the fastening body 21345 and the cover 21346, and coupled with the hooking protrusion 213471c of the moving member 21347 and then rotated forward, and a contacting part 21353 extended from the coupling part 21351 in an arc shape and having a tooth part 21353a formed at an end, and rotated forward together with the coupling part 21351 to be moved along the outer circumferential surface of the acetabular cup 2.

In this example, the coupling part 21351 may include a hooking protrusion coupling hole 21351c into which a hooking protrusion 213471c is inserted. The contacting part 21353 may be bent into a shape that corresponds to the outer circumferential surface of the acetabular cup 2 and the tooth part 21353a formed at the end of the contacting part 21353 may include a plurality of teeth formed along the end of the contacting part 21353.

As shown in FIG. 20, the coupling process of the coupling part 2134 and the blade 2135 will be described below. When inserting the blade 2135 into the slot 21346a, that is, when the blade 2135 is being inserted into the slot 21346a, the blade 2135 contacts the inclined surface (a) of the hooking protrusion 213471c protruding into the slot 21346a to press the hooking protrusion 213471c.

As shown in FIG. 21, as the hooking protrusion 213471c is pressed by the blade 2135, the hooking protrusion 213471c is placed in the guide groove 213453a of the fastening body 21345, and the moving member 21347, having the hooking protrusion 213471c on one side thereof, is slid along the guide groove 213453a toward the movement restricting member 21348 by a predetermined distance and at the same time, presses the elastic supporting member 21349 and the blade elastic supporting member 2134b into compressed state. At this time, the predetermined distance may correspond to the length by which the hooking protrusion 213471c protrudes into the slot 21346a.

Referring to FIG. 22, the elastic supporting member 21349 maintains being compressed by the moving member 21347, and when the hooking protrusion coupling hole 21351c of the blade 2135 is moved to a position corresponding to the hooking protrusion 213471c, that is, to a position where the hooking protrusion 213471c can be inserted into the hooking protrusion coupling hole 21351c, the elastic supporting member 21349 is elastically restored to the original state and thus presses the moving member 21347 toward the blade 2135. At this time, the blade elastic supporting member 2134b is still maintaining the compressed state.

Accordingly, the moving member 21347, which has been moved to the movement restricting member 21348 by a predetermined distance, is slid back to the blade 2135 and at the same time, the hooking protrusion 213471c provided on the moving member 21347 is inserted into the hooking protrusion coupling hole 21351c formed in the blade 2135 to fix the blade 2135.

Conversely, in the process of separating the coupling part 2134 and the blade 2135, as shown in FIGS. 23 and 24, the user presses the gripping projection 213473a provided on the moving member 21347 to move the moving member 21347 toward the movement restricting member 21348 and at the same time, presses the elastic supporting member 21349 to the compressed state. Accordingly, the hooking protrusion 213471c is spaced apart from the hooking protrusion coupling hole 21351c of the blade 2135 and the blade elastic supporting member 2134b, which has been kept in the compressed state under the pressure of the blade 2135, is elastically restored to the original state and presses the blade 2135 toward the direction opposite to the direction in which the blade 2135 is inserted.

Thus, the blade 2135, which has been fixed to a hooking protrusion 213471c, is separated from the hooking protrusion 213471c and thus released from the constraint of the fastening body 21345. At this time, the moving member 21347 that has been moved to the direction of the movement restricting member 21348 is returned to its original position as the elastic supporting members 21349 is elastically restored.

In the example described above, the coupling structure between the fastening part 2134 and the blade 2135 has been described. However, the coupling structure between the fastening part 2134 and the blade 2135 is not limited to the example provided above, and can be modified to more various structures.

Meanwhile, the pivoting cutter 21 of the acetabular cup detaching apparatus 1 in some embodiments may include a supporting cup 215 in a hemispheric shape which is coupled to the front end of the fixing part 211 and which is to be brought into close contact with the inner circumferential surface of the acetabular cup 2.

The supporting cup 215 is formed in a shape that corresponds to the inner circumferential surface of the acetabular cup 2, and is made of UHMW-PE resin having a polymer molecular weight of 3 million PM or above, and may serve as a lubricant between the acetabular cup 2 and the rotation part 213.

Meanwhile, the cutting part 20 may include a slide moving part 23.

Referring to FIG. 3, the slide moving part 23 is disposed slidably on the inner side of the rotary shaft part 11 and may be moved forward to rotate the pivoting cutter 21 at a predetermined angle while the rotary shaft part 11 is rotating.

More specifically, the slide moving part 23 may include a first slide moving part 231 disposed on the inner side of the rotary shaft part 11 and a second slide moving part 233 disposed on the outer side of the rotary shaft part 11. The first slide moving part 231 may be disposed on the inner side of the rotary shaft part 11 to be connected to an angle adjusting part 25 (to be described), and may be moved forward or backward along the inner surface of the rotary shaft part 11 according to the operation of the angle adjusting part 25. Further, the second slide moving part 233 may be disposed on the outer side of the rotary shaft part 11 to connect the first slide moving part 231 and the pivoting cutter 21 to each other, and when the first slide moving part 231 is rotated forward, the second slide moving part 233 may press the pivoting cutter 21 so that the pivoting cutter 21 is rotated.

Meanwhile, the second slide moving part 233 may include a supporting member 2331 and a pressing member 2333.

The supporting member 2331 may be disposed on the outer side of the rotary shaft part 11 and coupled with the first slide moving part 231 disposed on the inner side of the rotary shaft part 11, and when the first slide moving part 231 is moved forward or backward, the supporting member 2331 may be linearly moved along the outer circumferential surface of the rotary shaft part 11.

One side of the pressing member 2333 may be coupled to the pivoting cutter 21 and the other side is rotatably hinged to the supporting member 2331. Accordingly, when the supporting member 2331 is moved forward, the pressing member 2333 presses the pivoting cutter 21 so that the pivoting cutter 21 is rotated, while it 2333 is simultaneously rotated outward by the angle of rotation of the pivoting cutter 21.

Further, the cutting part 20 may include an angle adjusting part 25.

Figure 10:
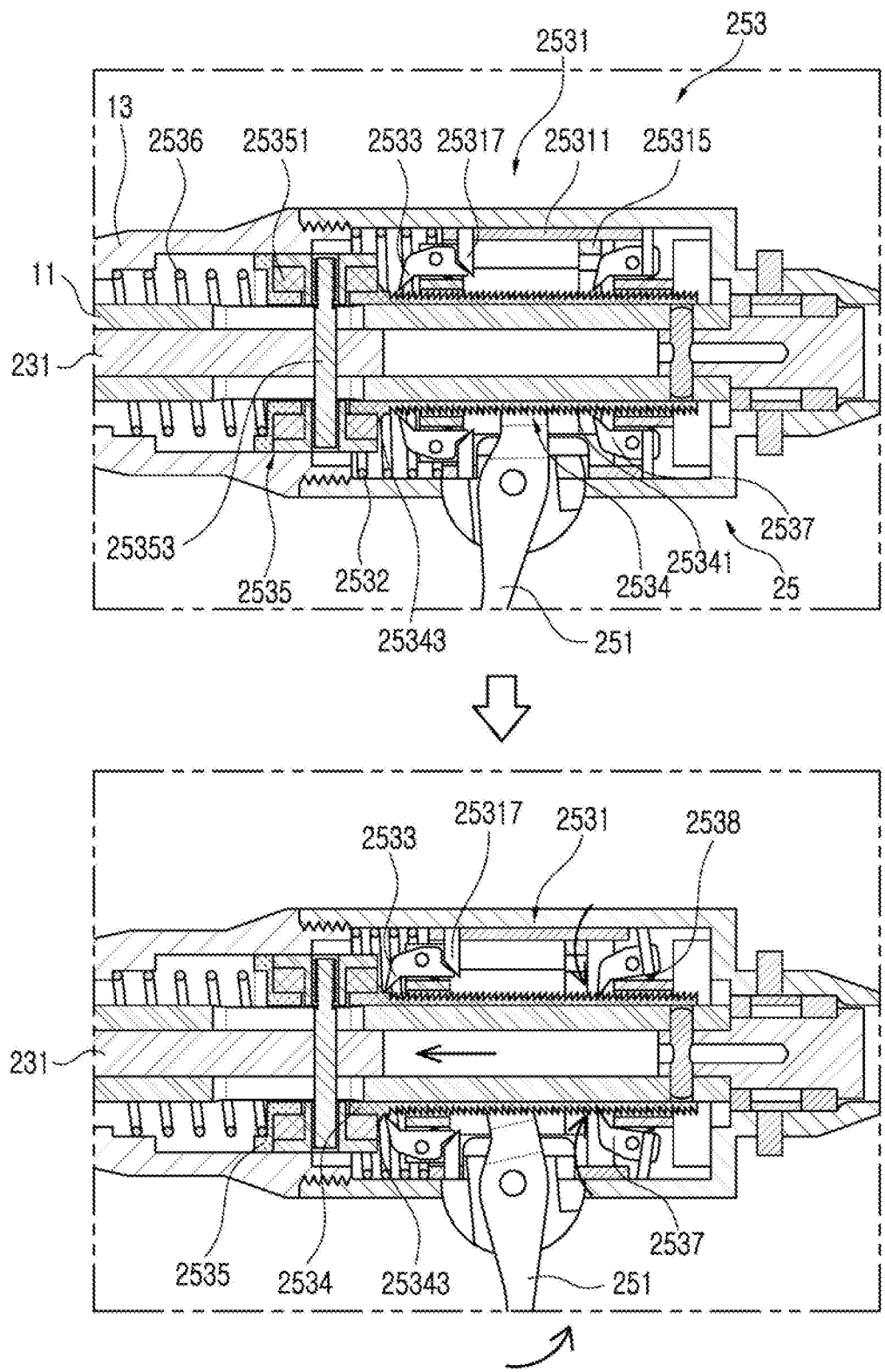
FIGS. 10 to 14 are views showing a process of adjusting the angle of an acetabular cup detaching apparatus for an artificial hip joint according to an embodiment.

Referring to FIGS. 3 and 10, the angle adjusting part 25 may be disposed on the inner side of the housing part 13 to adjust the angle of rotation of the pivoting cutter 21 by sliding the slide moving part 23 by a predetermined distance.

More specifically, the angle adjusting part 25 may include an adjusting lever 251 rotatably disposed on the inner side of the housing part 253 to be rotated forward or backward, and an adjusting part 253 to be moved forward in a stepwise manner according to the rotation of the adjusting lever 251 to rotate the pivoting cutter 21 at a predetermined angle.

More specifically, as shown in FIGS. 10 to 14, the adjusting lever 251 may be rotatably formed by being hinged to the housing part 13 and may be connected to the adjusting part disposed on the inner side of the housing part 13 by an assembling pin 25313 to be described below, to change the rotary motion into linear motion.

The adjusting part may have such a structure that can be moved forward or returned backward in a stepwise manner according to the rotation of the adjusting lever 251.

More specifically, the adjusting part may include a plurality of moving parts (first moving part 2531, second moving part 2534, third moving part 2535) linearly moved forward according to the rotation of the adjusting lever 251 to rotate the pivoting cutter 21 or linearly moved backward to return the pivoting cutter 21 to its original position, a plurality of elastic members (first elastic member 2532, second elastic member 2536) for applying a repulsive force to the plurality of moving parts, and a plurality of hooks (moving hook 2533, fixing hook 2537) for moving the plurality of moving parts forward and supporting the plurality of moving parts after the plurality of moving parts are moved forward.

Figure 15:
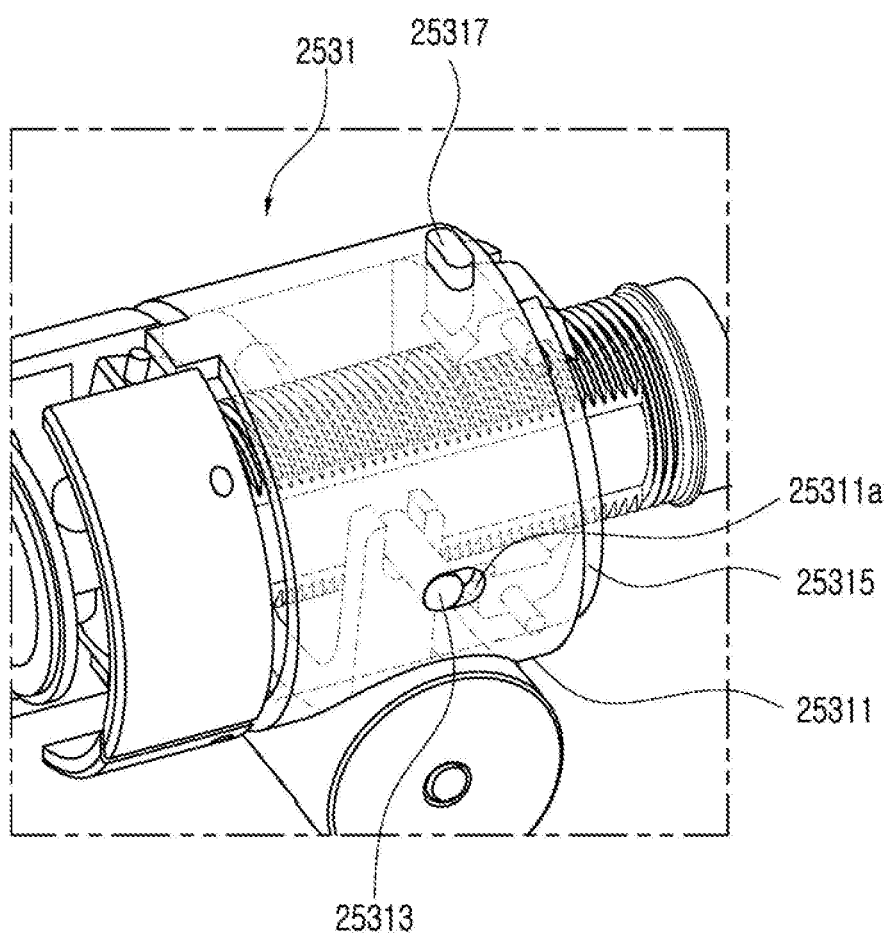
FIG. 15 is a perspective view schematically showing a first moving part of an acetabular cup detaching apparatus for an artificial hip joint according to an embodiment.

The first moving part 2531 may be connected to the adjusting lever 251 and linearly moved forward when the adjusting lever 251 is rotated backward and linearly moved backward when the adjusting lever 251 is rotated forward. Specifically, as shown in FIG. 15, the first moving part 2531 may be disposed on the inner circumferential surface of the housing part 13, and may include, in the outer circumferential surface, a first sliding part 25311 having a movement restricting slot 25311a into which the assembling pin 25313 for connecting the adjusting lever 251 and the first moving part 2531 to each other is inserted to limit the movement of the first moving part 2531; a second sliding part 25315 disposed inside the first sliding part 25311 and connected to the first sliding part 25311 by the assembling pin 25313 for integrated operation, and having a moving hook 2533 formed at a front side to be described below; and a stopper 25317 provided on the first sliding part 25311 to support the moving hook 2533.

The first elastic member 2532 may be disposed on a front portion of the first moving part 2531 to elastically support the first moving part 2531, and when the force that rotates the adjusting lever 251 is ceased after the first moving part 2531 is moved forward, the first elastic member 2532 may apply a repulsive force to the first moving part 2531 so that the first moving part 2531 is moved backward.

The second moving part 2534 may be disposed on the outer circumferential surface of the rotary shaft part 11 and may have a plurality of hooking projections 25341 formed along a lengthwise direction thereof. Specifically, the second moving part 2534 may be disposed between the first moving part 2531 and the rotary shaft part 11, and may include, on the outer circumferential surface of the second moving part 2534, a supporting projection 25343 and a plurality of hooking projections 25341 to support the third moving part 2535, which may be hooked with the moving hook 2533 and supported before the moving hook 2533 is separated from the stopper 25317. In this example, the supporting projection 25343 may be formed closer to outside than the plurality of hooking projections 25341. That is, in an initial state in which the moving hook 2533 is in close contact with the stopper 25317 and maintains a horizontal position, when the first moving part 2531 is moved forward, the second moving part 2534 may be moved while being supported on the supporting projection 25343 that is formed closer to outside than the hooking projections 25341. Then, when the first moving part 2531 that has completed the first movement is moved forward again, since the moving hook 2533 has been spaced away from the stopper 25317 and rotated inward, the second moving part 2534 may be moved while being supported on one of the plurality of hooking projections 25341. In addition, the hooking projection 25341 may have an inclined surface on the front side, and a vertical surface on the rear side. Accordingly, when the moving hook 2533 is moved forward, the moving hook 2533 may be moved in contact with the vertical surface of the hooking projection 25341, while, when the moving hook 2533 is moved backward, the moving hook 2533 may be moved along the inclined surface of the hooking projection 25341.

The moving hook 2533 may be rotatably formed on the first moving part 2531 such that, when the adjusting lever 251 is rotated backward, the moving hook 2533 may support the second moving part 2534 so that the second moving part 2534 is moved forward, while the moving hook 2533 may be separated from the second moving part 2534 when the adjusting lever 251 is rotated forward. Specifically, the moving hook 2533 may be rotatably provided on the first moving part 2531 so that the moving hook 2533 may be rotated into contact with the outer circumferential surface of the second moving part 2534 or rotated away from the outer circumferential surface of the second moving part 2534, while the moving hook 2533 may be supported by the stopper 25317 to be held in a horizontal position, and also elastically supported by an auxiliary elastic member 2538 provided between the moving hook 2533 and the first moving part 2531 such that, when separated from the stopper 25317, the moving hook 2533 may be rotated by the elastic force of the auxiliary elastic member 2538 and brought into contact with the second moving part 2534.

The third moving part 2535 may be supported by the second moving part 2534 and moved forward together with the second moving part 2534, while simultaneously connected to the slide moving part 23 to move the slide moving part 23 forward. Specifically, the third moving part 2535 may include a connecting part 25351 provided on the outer side of the rotary shaft part 11, and a connecting pin 25353 passed through the connecting part 25351, the rotary shaft part 11 and the slide moving part 23 to connect the connecting part 25351 and the slide moving part 23.

The second elastic member 2536 may be disposed in front of the third moving part 2535 to elastically support the third moving part 2535, and move the second moving part 2534 and the third moving part 2535 backward by applying a repulsive force to the third moving part 2535 when the adjusting lever 251 is rotated forward.

The fixing hook 2537 may be rotatably provided on the housing part 13 and positioned behind the second moving part 2534, and may support the second moving part when the adjusting lever 251 is rotated backward, and may be separated from the second moving part 2534 when the adjusting lever 251 is rotated forward, as it 2537 is supported by the end of the first moving part 2531 and changed into a horizontal position. That is, the fixing hook 2537 may be supported by the first moving part 2531 and maintain the horizontal position, and may be rotated by the elastic force of the auxiliary elastic member 2538 and brought into contact with the second moving part 2534 when the fixing hook 2537 is elastically supported by the auxiliary elastic member 2538 provided between the fixing hook 2537 and the housing part 13 and separated from the first moving part 2531.

Meanwhile, the body part 10 may further include a handle part 15 that can be gripped, and a power part 17 coupled to the rotary shaft part 11 to transmit power to the rotary shaft part 11.

Referring to FIG. 3, the handle part 15 may include a clamp 151 provided on the outer circumferential surface of the rotary shaft part 11 and movable along the outer circumferential surface of the rotary shaft part 11, and a locking nut 153 fastened to an end of the clamp 151 to fix the clamp 151 and limit the movement of the clamp 151.

The clamp 151 may include a cage 1511 surrounding a perimeter of the rotary shaft part 11, a movement restricting part 1513 disposed on the inner side of the cage 1511 and brought into close contact with the outer circumferential surface of the rotary shaft part 11 to restrict the movement of the clamp 151 when the locking nut 153 is fastened, and a bearing 1515 disposed on the inner side of the cage 1511 to support the rotary shaft part 11.

For example, the movement restricting part 1513 may include an anchor 15131 disposed on the outer circumferential surface of the rotary shaft part 11 and made of a porous material having a plurality of through holes formed along the circumference thereof so that it 1513 is compressed by an external force and brought into close contact with the rotary shaft part 11, and a pressing block 15133 disposed at both ends of the anchor 15131 and pressed against the cage 1511 that is compressed inward upon fastening of the locking nut 153 to thus press the anchor 15131.

Meanwhile, the handle part 15 may further include an auxiliary handle 155.

Referring to FIGS. 2 and 3, the auxiliary handle 155 may include a clamp ring 1551 for surrounding the perimeter of the handle part 15 when rotated, and a grip 1553 fastened to the clamp ring 1551.

In one example, the clamp ring 1551 may be a rotatable structure formed by semicircular rings hinged together, and may include a semi-cylindrical bolt formed on one side of each of the rings. Accordingly, when the clamp ring 1551 is surrounding the handle 15, the grip 1553 can be completely fixed to the handle part 15 by being fastened with and tightening the bolts of the respective rings that are formed at predetermined intervals from each other.

Figure 16:
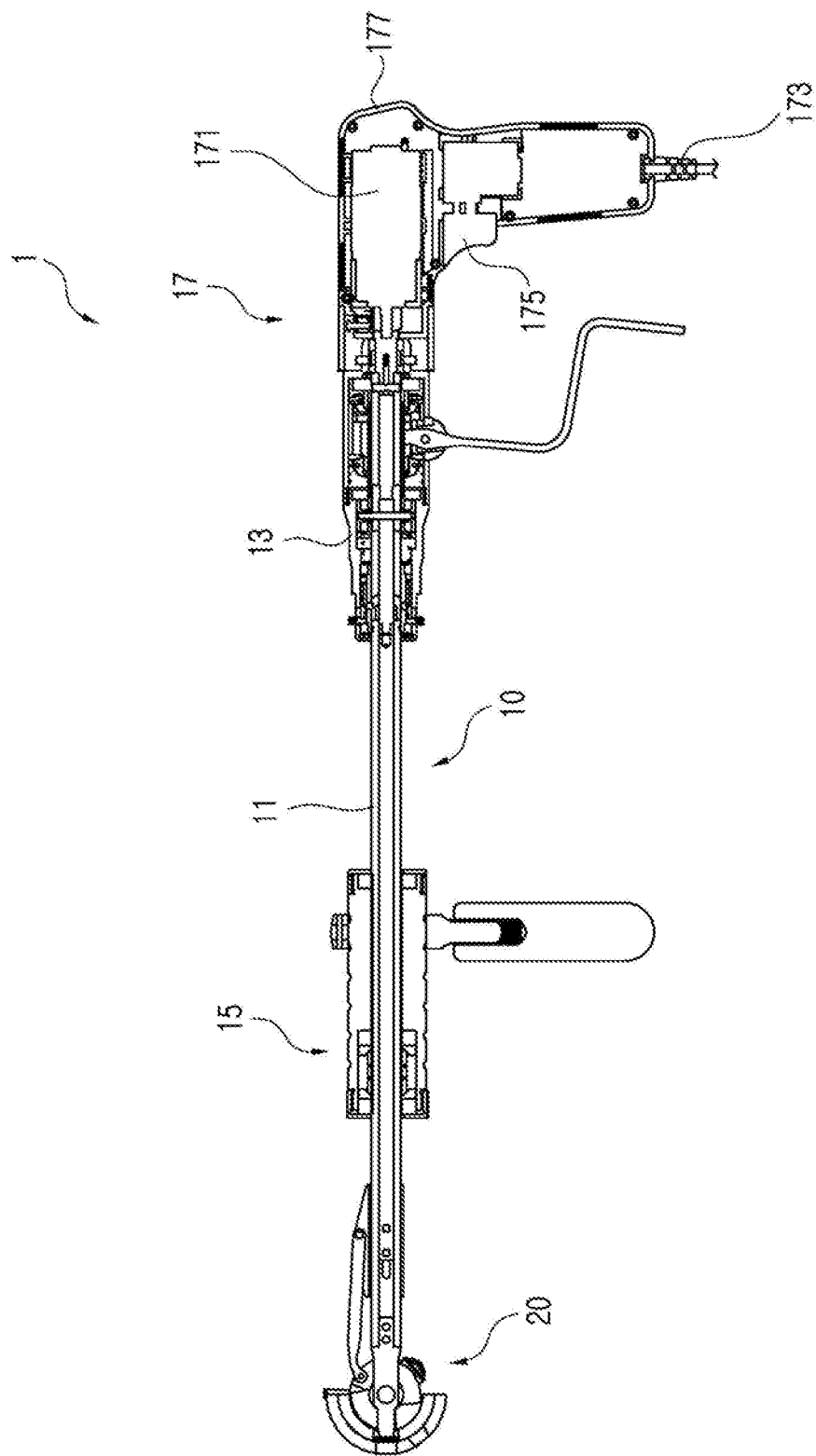
FIG. 16 is a cross-sectional view schematically showing a state in which a power part is coupled to an acetabular cup detaching apparatus for an artificial hip joint according to an embodiment.

Referring to FIG. 16, the power part 17 may include a motor 171 coupled to the rotary shaft part 11 to provide power, a power supply 173 to supply power to the motor 171, a control button 175 to control the operation of the motor 171 and a housing 177 to receive the motor 171 and the control button 175. Therefore, the torque and the direction of rotation of the motor 171 can be controlled.

In one example, the power supply 173 may be provided as a cable or a rechargeable battery that supplies power.

Hereinafter, the angle adjustment process will be described.

Figure 11:
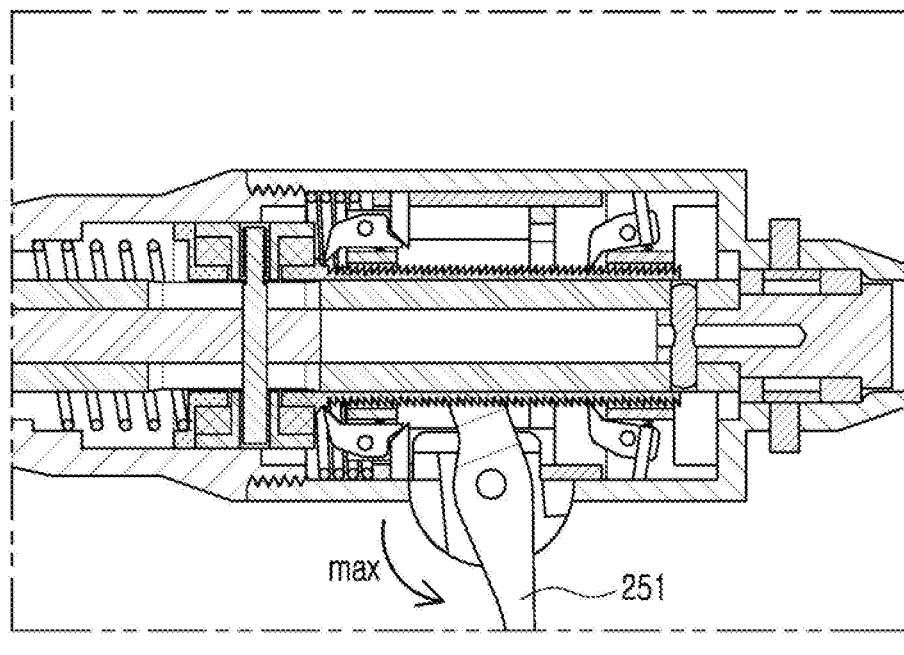
Figure 11:
Figure 11:
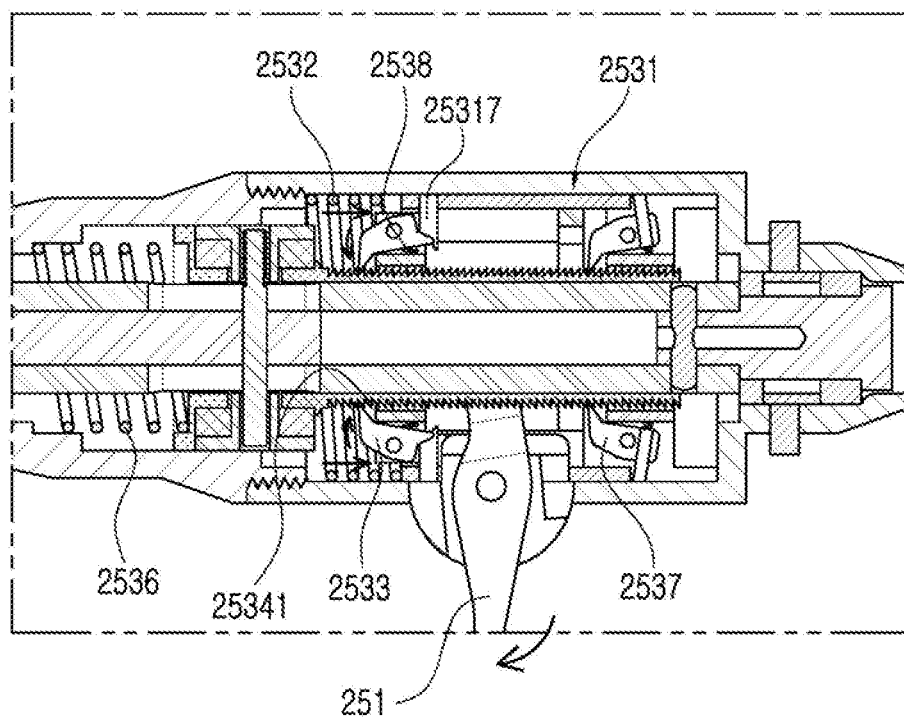

Referring to FIGS. 10 and 11, when the adjusting lever 251 is rotated backward from the initial state by a predetermined angle, the first moving part 2531 coupled to the adjusting lever 251 is moved forward, and along with this, the moving hook 2533 is brought into contact with the supporting projection 25343 of the second moving part 2534 and presses the second moving part 2534 forward. At this time, the moving hook 2533 that moves together with the adjusting lever 251 may be supported by the stopper 25317 and placed in a horizontal position, and the fixing hook 2537 may be pressed against the auxiliary elastic member 2538 and pivoted inward as the first moving part 2531 is moved forward.

When the adjusting lever 251 is pivoted to the maximum point and the force that presses the adjusting lever 251 is ceased, the first moving part 2531 is moved backward by the elastic restoring force of the first elastic member 2532 disposed in front of the first moving part 2531. At this time, the moving hook 2533 is spaced apart from the stopper 25317 by a predetermined distance, whereby the moving hook 2533 is pivoted inward and moved backward along the inclined surface formed on the hooking projection 25341 of the second moving part 2534 while maintaining contact with the outer surface of the second moving part 2534, and at the same time, the fixing hook 2537 supports the second moving part 2534 that has been moved forward in contact with the engaging step 25341 of the second moving part 2534.

Accordingly, the first angle adjustment step is completed.

Figure 12:
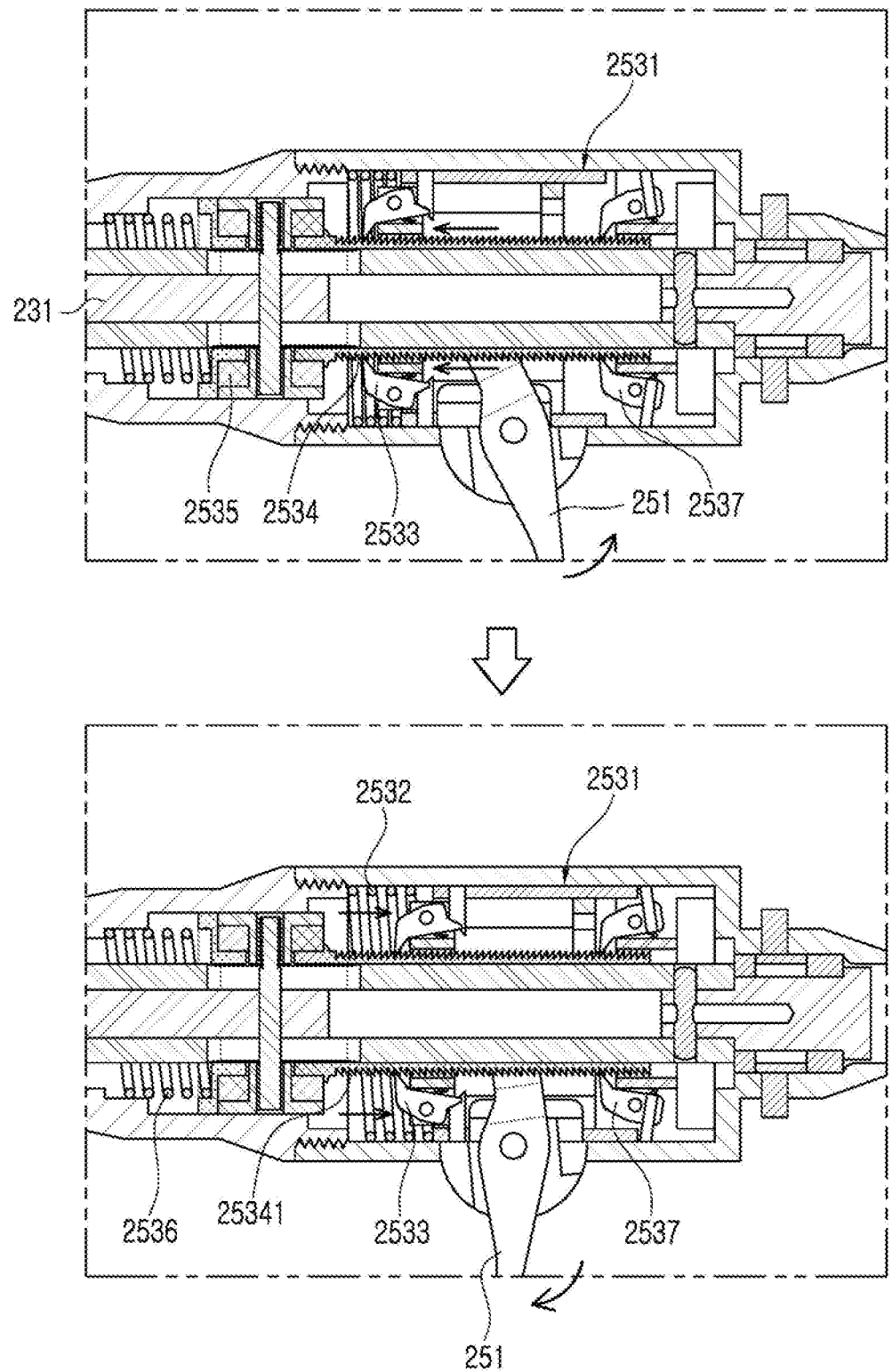

Referring to FIG. 12, after completing the first angle adjustment step, the adjusting lever 251 returned to the initial position is rotated backward again by a predetermined angle.

As a result, the first moving part 2531 is moved forward and along with this, the moving hook 2533 is supported by the hooking projection 25341 of the second moving part 2534 to thus move the second moving part 2534 and the third moving part 2536 forward.

When the adjusting lever 251 is pivoted to the maximum point and the force that presses the adjusting lever 251 is ceased, likewise the first angle adjustment step, the first moving part 2531 is moved backward by the elastic restoring force of the first elastic member 2532, and the adjusting lever 251 is returned to the initial position, and the fixing hook 2537 supports the second moving part 2534 so that the second moving part 2534 maintains its position after being moved forward.

Accordingly, the second angle adjustment step is completed.

Figure 13:
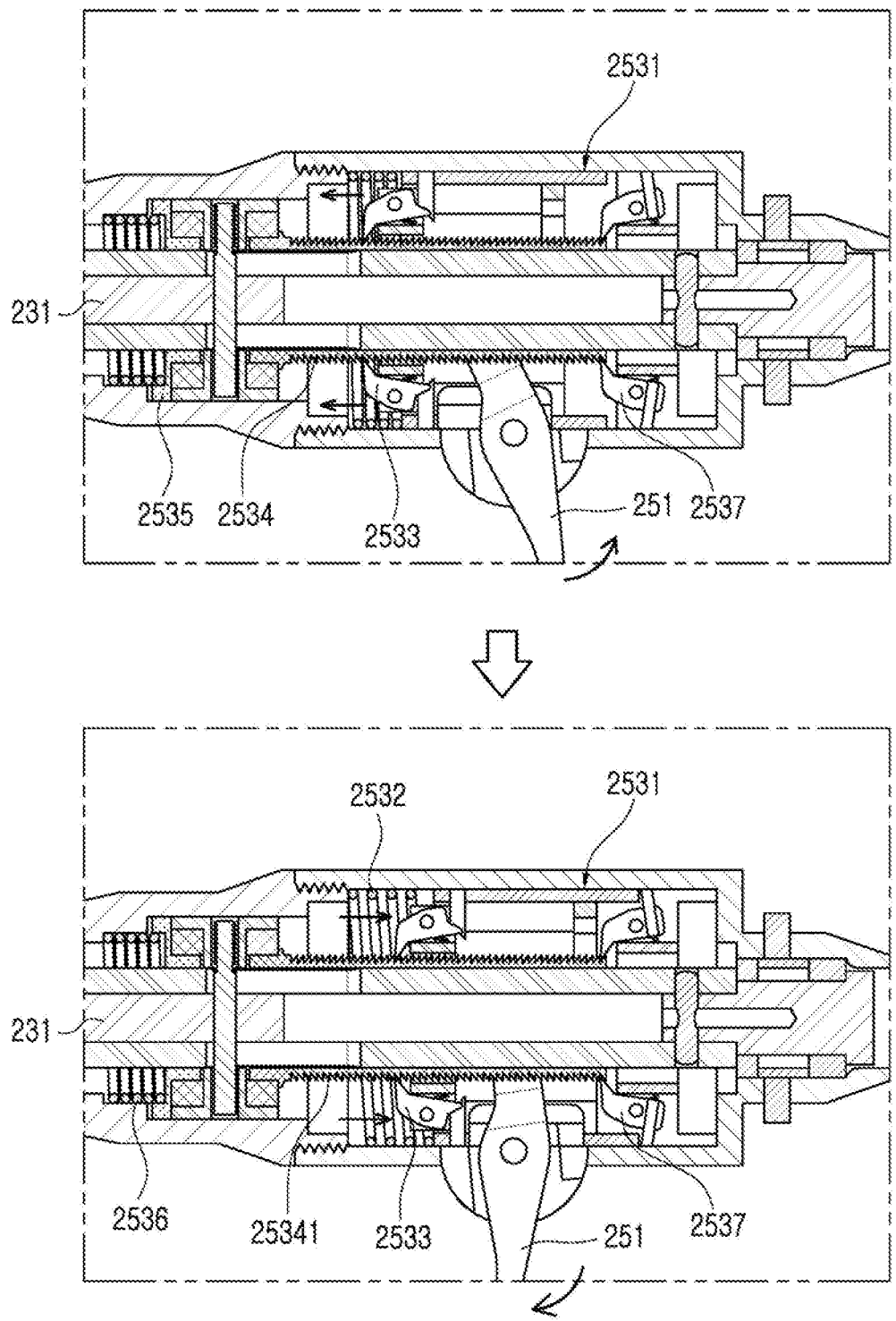

Referring to FIG. 13, after completing the second angle adjustment step, the adjusting lever 251 returned to the initial position is rotated backward again by a predetermined angle.

As a result, the first moving part 2531 is moved forward again, and along with this, the moving hook 2533 is supported at another position of the hooking projection 25341 of the second moving part 2534, to thus move the second moving part 2534 and the third moving part 2536 forward.

When the adjusting lever 251 is pivoted to the maximum point and the force that presses the adjusting lever 251 is ceased, likewise the second angle adjustment step, the first moving part 2531 is moved backward by the elastic restoring force of the first elastic member 2532, and the adjusting lever 251 is returned to the initial position, and the fixing hook 2537 supports the second moving part 2534 so that the second moving part 2534 maintains its position after being moved forward.

Accordingly, the third angle adjustment step is completed.

Figure 14:
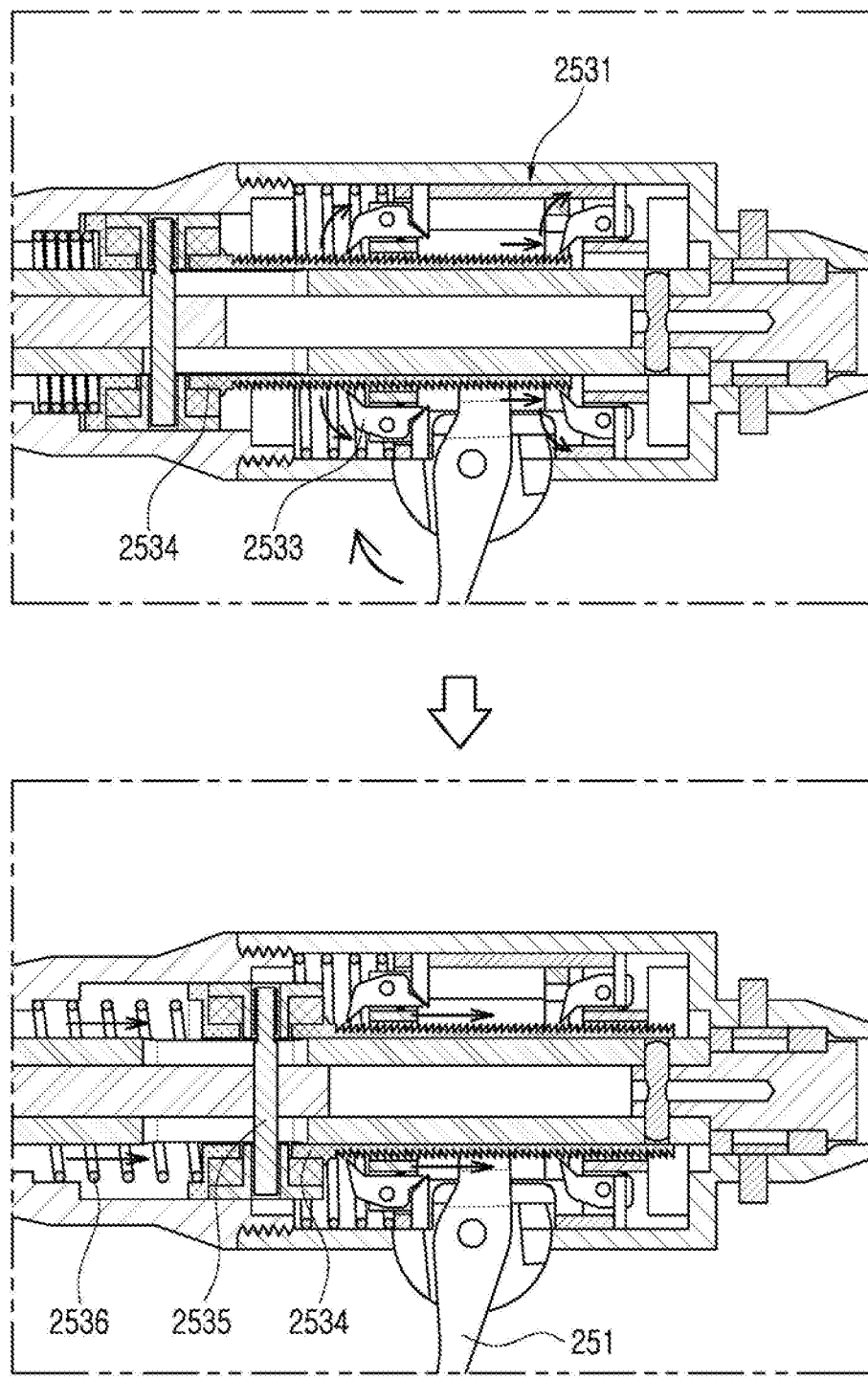

Referring to FIG. 14, after completing the third angle adjustment step, the adjusting lever 251 returned to the initial position is rotated forward by a predetermined angle.

As the adjusting lever 251 is rotated forward by a predetermined angle, the first moving part 2531 may be moved backward and brought into close contact with the moving hook 2533 and the fixed hook 2537, and the moving hook 2533 and the fixed hook 2537 may be outwardly pivoted away from the contact with the outer circumferential surface of the second moving part 2534 and changed to the horizontal position. Also, at the same time, the force that supports the second moving part 2534 is ceased such that the second elastic member 2536 in the compressed state in front of the third moving part 2535 moves the second moving part 2534 and the third moving part 2535 backward with the elastic restoring force.

Accordingly, the acetabular cup detaching apparatus 1 for the artificial hip joint is restored to its initial state.

According to the present invention, the blade 2135 is rotated together with the rotary shaft part 11 in the radial direction of the acetabular cup 2 and at the same time, the blade 2135 is rotated along the outer circumferential surface of the acetabular cup 2 through the electric control. Accordingly, it is possible to detach the acetabular cup 2 from the acetabular bone quickly and accurately irrespective of the skill of the operator.

In addition, the supporting cup 215 and the blade 2135 are formed to have sizes corresponding to the outer circumferential surface and the inner circumferential surface of the acetabular cup 2, and the blade 2135 is rotated by a predetermined angle by predetermined steps, to gradually cut the acetabular bone part to which the acetabular cup 2 is attached, and as a result, it is possible to prevent breakage of the blade 2135, and also accurately detach only the acetabular cup 2 from the acetabular bone while minimizing the damage of the acetabular bone.

Further, a slide moving part 23, which is linearly movable, is provided on the inner side of the rotary shaft part 11 rotated in a radial direction of the acetabular cup 2, and the slide moving part 23 is moved forward by predetermined steps through the rotation of the lever to adjust the angle of rotation of the blade 2135. As a result, the user is able to easily rotate the blade 2135 along the surface of the acetabular cup 2 even during a rotation of the rotary shaft part 11, and the simplified arrangement of the structure reduces the restriction of the space required at the time of detaching acetabular cup 2, thereby minimizing the interference with surrounding body tissues.

The present disclosure has been described in detail. However, it should be understood that the detailed description and specific examples, while indicating preferred embodiments of the disclosure, are given by way of illustration only, since various changes and modifications within the scope of the disclosure will become apparent to those skilled in the art from this detailed description.

INDUSTRIAL APPLICABILITY

An acetabular cup detaching apparatus for an artificial hip joint according to embodiments of the present disclosure can be used in an operation for replacing the acetabular cup of the artificial hip joint.

What is claimed is:

1. An acetabular cup detaching apparatus for an artificial hip joint comprising:
a body part that rotates with power transmitted thereto; and
a cutting part configured to be brought into close contact with an inner circumferential surface of the acetabular cup and rotating together with the body part to cut a surface of an acetabular bone to which an acetabular cup is attached,
wherein the body part comprises:
a rotary shaft part formed in a tubular shape that is rotated with power transmitted thereto and having the cutting part coupled to one side; and
a housing part surrounding a perimeter of the rotary shaft part, and wherein the cutting part comprises:
a pivoting cutter coupled to the rotary shaft part and configured to be brought into close contact with an inner circumferential surface of the acetabular cup, rotated together with the rotary shaft part in a radial direction of the acetabular cup, and simultaneously rotated along an outer circumferential surface of the acetabular cup to cut a surface of the acetabular bone to which the acetabular cup is attached;
a slide moving part disposed slidably on an inner side of the rotary shaft part and moved forward to rotate the pivoting cutter by a predetermined angle while the rotary shaft part is rotating; and
an angle adjusting part disposed within the housing part to cause the slide moving part to be slide by a predetermined distance and adjust an angle of rotation of the pivoting cutter.

2. The acetabular cup detaching apparatus of claim 1, wherein the pivoting cutter comprises:
a fixing part coupled to a front end of the rotary shaft part;
a pivoting part rotatably coupled to the fixing part; and
a supporting cup coupled to a front end of the fixing part and configured to be brought into close contact with an inner circumferential surface of the acetabular cup.

3. The acetabular cup detaching apparatus of claim 2, wherein the pivoting part comprises:
a pivoting axis disposed to pass through the fixing part and intersect with a center axis of the fixing part;
a pivoting member coupled to the fixing part, with the fixing part being passed through the pivoting shaft from a first side to a second side of the fixing part, such that the pivoting member is rotatably disposed between the supporting cup and the fixing part, wherein the pivoting member has a rotation guide slot formed in a direction of rotation;
a side cover coupled to each of the first side and the second side of the fixing part of the pivoting member and rotated together with the pivoting member;
a fastening part disposed between the pivoting member and the side cover disposed on both sides of the pivoting member respectively, and rotated together with the side cover; and
a blade coupled to the fastening part and rotated together with the fastening part.

4. The acetabular cup detaching apparatus of claim 3, wherein the fastening part comprises:
a supporting plate supported by the side cover;
a fastening piece protruding outward from an outer surface of the supporting plate, and having a seating groove formed on an inner side on which the blade is seated and a screw thread formed on an outer side;
a locking pin passed through the fastening piece; and
a fastening nut fastened to the fastening piece to fix the blade.

5. The acetabular cup detaching apparatus of claim 4, wherein the blade comprises:

a coupling part inserted into the fastening piece along a vertical direction with respect to a center axis of the rotary shaft part, and seated in the seating groove and then rotated forward; and a contacting part extending in an arc shape from the coupling part and comprising a tooth part formed at an end thereof, the contacting part being rotated forward together with the coupling part.

6. The acetabular cup detaching apparatus of claim 5, wherein the coupling part comprises a first coupling groove to which the locking pin is inserted when the coupling part is inserted into the fastening piece, and a second coupling groove on which the locking pin disposed in the first coupling groove is seated when the coupling part is rotated forward.

7. The acetabular cup detaching apparatus of claim 3, wherein the fastening part comprises:

a fastening body disposed between the pivoting member and the side cover, and having a guide groove formed therein;

a cover coupled to one side of the fastening body to form a slot into which the blade can be inserted;

a moving member coupled to the guide groove, wherein, when the blade is inserted into the slot, the moving member is pressed against the blade, moved along the guide groove toward the rotary shaft part, and then slid toward the blade and coupled to the blade;

a movement restricting member coupled to another side of the fastening body to restrict the movement of the moving member; and an elastic supporting member disposed between the moving member and the movement restricting member and resiliently supporting the moving member toward the slot.

8. The acetabular cup detaching apparatus of claim 7, wherein the fastening parts comprises:

a fixing pin to fix the moving member and the movement restricting member to the fastening body; and a blade elastic supporting member provided on the fixing pin to elastically support the blade, wherein, when the moving member that fixes the blade is separated away from the blade, the blade elastic supporting member is decompressed to thus press and move the blade in a direction opposite to a direction in which the blade has been inserted.

9. The acetabular cup detaching apparatus of claim 8, wherein the fastening body comprises:

a supporting plate supported by the side cover; and a guide part protruding outward from an outer surface of the support plate, and comprising, on an inner side, the guide groove, a receiving groove for receiving the blade elastic supporting member, and a blade elastic supporting member insertion hole communicating with the receiving groove and into which the one side of the blade elastic supporting member is inserted, and also comprising, on an outer side, a plurality of pin fastening holes passed through the guide groove and the receiving groove.

10. The acetabular cup detaching apparatus of claim 8, wherein the moving member comprises:

a first moving part seated in the guide groove and moved along the guide groove; and a second moving part seated on an end of the fastening body and moved along the fastening body when the first moving part is moved.

11. The acetabular cup detaching apparatus of claim 10, wherein the first moving part comprises a movement restricting slot through which the fixing pin is passed, and an elastic supporting member insertion groove into which one side of the elastic supporting member is inserted, and a hooking protrusion formed on one side of the first moving part that faces the blade to fix the blade within the slot, wherein the hooking protrusion includes an inclined surface formed on one side.

12. The acetabular cup detaching apparatus of claim 11, wherein the blade comprises:

a coupling part inserted into the slot and fixed with the hooking protrusion and then rotated forward; and a contacting part extending in an arc shape from the coupling part and comprising a tooth part formed at an end thereof, the contacting part being rotated forward together with the coupling part.

13. The acetabular cup detaching apparatus of claim 12, wherein the coupling part comprises a hooking protrusion coupling groove into which the hooking protrusion is inserted.

14. The acetabular cup detaching apparatus of claim 10, wherein the second moving part comprises a gripping protrusion protruding outward from an end thereof to form a projection.

15. The acetabular cup detaching apparatus of claim 8, comprising:

a through hole formed on an inner side of the movement restricting member through which the fixing pin is passed; and an elastic supporting member seating groove formed on one side of the movement restricting member that faces the moving member, the elastic supporting member being inserted into and seated on the elastic supporting member seating groove, and a movement restricting protrusion protruding from an end of the second moving part by a predetermined length to limit a maximum movement distance of the moving member.

16. The acetabular cup detaching apparatus of claim 1, wherein the slide moving part comprises:

a first slide moving part disposed on an inner side of the rotary shaft part and connected to the angle adjusting part, and moved forward or backward along an inner surface of the rotary shaft part according to an operation of the angle adjusting part; and a second slide moving part disposed on an outer side of the rotary shaft part and connecting the first slide moving part and the pivoting cutter to each other, and pressing the pivoting cutter upon a forward movement of the first slide moving part so that the pivoting cutter is rotated.

17. The acetabular cup detaching apparatus of claim 16, wherein the second slide moving part comprises:

a supporting member coupled to the first slide moving part and linearly moved along an outer circumferential surface of the rotary shaft part; and a pressing member of which one side is coupled to the pivoting cutter and another side is rotatably coupled to the supporting member, so as to press the pivoting cutter upon a forward movement of the supporting member so that the pivoting cutter is rotated, while simultaneously being rotated outward by an angle corresponding to an angle of rotation of the pivoting cutter.

18. The acetabular cup detaching apparatus of claim 1, wherein the angle adjusting part comprises:

an adjusting lever rotatably disposed on an inner side of the housing part to be rotated forward or backward; and an adjusting part moved forward according to steps according to a rotation of the adjusting lever to rotate the pivoting cutter by a predetermined angle.

19. The acetabular cup detaching apparatus of claim 18, wherein the adjusting part comprises:
   a first moving part connected to the adjusting lever, wherein the first moving part is linearly moved forward when the adjusting lever is rotated backward and linearly moved backward when the adjusting lever is rotated forward;
   a first elastic member disposed in front of the first moving part to elastically support the first moving part;
   a second moving part disposed on an outer circumferential surface of the rotary shaft part and having a plurality of hooking projections formed along a lengthwise direction;
   a moving hook rotatably provided on the first moving part to support and move the second moving part forward when the adjusting lever is rotated backward, wherein the moving hook is separated away from the second moving part when the adjusting lever is rotated forward;
   a third moving part supported by the second moving part and moved forward together with the second moving part, and at the same time, connected to the slide moving part to move the slide moving part forward;
   a second elastic member disposed in front of the third moving part to elastically support the third moving part; and
   a fixing hook rotatably provided on the housing part to support the second moving part when the adjusting lever is rotated backward, wherein the fixing hook is separated from the second moving part when the adjusting lever is rotated forward.

20. The acetabular cup detaching apparatus of claim 19, wherein the first moving part comprises:
   a first sliding part disposed on an inner circumferential surface of the housing part and having a movement restricting slot formed on an outer circumferential surface into which an assembling pin for connecting the adjusting lever and the first moving part to each other is inserted;
   a second sliding part disposed on an inner side of the first sliding part and integrally operated with the first sliding part, and having the moving hook disposed on a front side thereof; and
   a stopper provided on the first sliding part to support the moving hook.

21. The acetabular cup detaching apparatus of claim 20, wherein the moving hook is supported by the stopper and held in a horizontal position, and elastically supported with an auxiliary elastic member provided between the moving hook and the first moving part, wherein, when the moving hook is spaced away from the stopper, the moving hook is rotated by an elastic force of the auxiliary elastic member and brought into contact with the second moving part.

22. The acetabular cup detaching apparatus of claim 20, wherein the second moving part comprises, on an outer circumferential surface, a supporting projection and the plurality of hooking projections, which support the third moving part and which are hooked on the moving hook before the moving hook is separated from the stopper.

23. The acetabular cup detaching apparatus of claim 19, wherein the third moving part comprises:
   a connecting part provided on an outer side of the rotary shaft part; and
   a connecting pin passed through the connecting part, the rotary shaft part, and the slide moving part to connect the connecting part and the slide moving part.

24. The acetabular cup detaching apparatus of claim 19, wherein the fixing hook is supported by the first moving part and held in a horizontal position, and elastically supported with an auxiliary elastic member provided between the fixing hook and the housing part, wherein, when the fixing hook is spaced away from the first moving part, the fixing hook is rotated by an elastic force of the auxiliary elastic member and brought into contact with the second moving part.

25. The acetabular cup detaching apparatus of claim 1, wherein the body part comprises a handle part that can be gripped.

26. The acetabular cup detaching apparatus of claim 25, wherein the handle part comprises:
   a clamp provided on an outer circumferential surface of the rotary shaft part; and
   a locking nut fastened to an end of the clamp to fix the clamp.

27. The acetabular cup detaching apparatus of claim 26, wherein the clamp comprises:
   a cage surrounding a perimeter of the rotary shaft part;
   a movement restricting part disposed on an inner side of the cage and brought into close contact with an outer circumferential surface of the rotary shaft part to limit a movement of the clamp when the locking nut is fastened; and
   a bearing disposed on an inner side of the cage to support the rotary shaft part.

28. The acetabular cup detaching apparatus of claim 27, wherein the movement restricting part comprises:
   an anchor disposed on the outer circumferential surface of the rotary shaft part and pressed and brought into close contact with the rotary shaft part when an external force is applied; and
   a pressing block disposed at opposite ends of the anchor and pressing the anchor when the locking nut is fastened.

29. The acetabular cup detaching apparatus of claim 27, wherein the handle part further comprises an auxiliary handle.

30. The acetabular cup detaching apparatus of claim 29, wherein the auxiliary handle comprises:
   a clamp ring that surrounds a perimeter of the handle part upon being rotated; and
   a grip fastened to the clamp ring.

31. The acetabular cup detaching apparatus of claim 1, wherein the body part further comprises a power part coupled to the rotary shaft part to transmit power to the rotary shaft part.

32. The acetabular cup detaching apparatus of claim 31, wherein the power part comprises:
   a motor coupled to the rotary shaft part to provide power;
   a power supply to supply power to the motor;
   a control button to control an operation of the motor; and
   a housing to receive the motor and the control button therein.

* * * * *